US007601489B2

(12) United States Patent
Boeke et al.

(10) Patent No.: US 7,601,489 B2
(45) Date of Patent: Oct. 13, 2009

(54) MANGANESE ION REGULATION OF REVERSE TRANSCRIPTASE ACTIVITY AND METHODS OF MODULATING SAME

(75) Inventors: Jef D. Boeke, Baltimore, MD (US); Eric C. Bolton, San Francisco, CA (US)

(73) Assignee: The Johns Hopkins University, Baltimore, MD (US)

( * ) Notice: Subject to any disclaimer, the term of this patent is extended or adjusted under 35 U.S.C. 154(b) by 317 days.

(21) Appl. No.: 10/507,252

(22) PCT Filed: Mar. 12, 2003

(86) PCT No.: PCT/US03/07879

§ 371 (c)(1), (2), (4) Date: Jan. 28, 2005

(87) PCT Pub. No.: WO03/078650

PCT Pub. Date: Sep. 25, 2003

(65) Prior Publication Data
US 2005/0123624 A1 Jun. 9, 2005

Related U.S. Application Data

(60) Provisional application No. 60/363,708, filed on Mar. 12, 2002.

(51) Int. Cl.
*C12Q 1/00* (2006.01)
*C12Q 1/48* (2006.01)
(52) U.S. Cl. ............................................. 435/4; 435/15
(58) Field of Classification Search ...................... None
See application file for complete search history.

(56) References Cited

U.S. PATENT DOCUMENTS

| | | | |
|---|---|---|---|
| 5,206,347 A | 4/1993 | Ruoslahti et al. | |
| 5,225,212 A | 7/1993 | Martin et al. | |
| 5,264,563 A | 11/1993 | Huse | |
| 5,314,695 A | 5/1994 | Brown | |
| 5,395,619 A | 3/1995 | Zalipsky et al. | |
| 5,622,699 A | 4/1997 | Ruoslahti et al. | |
| 5,750,342 A | 5/1998 | Stephens et al. | |
| 5,882,679 A | 3/1999 | Needham | |

OTHER PUBLICATIONS

Wei Y et at (2000) Phenotypic screening of mutations in Pmr1, the yeast secretory pathway Ca2+/Mn2+-ATPase, reveals residues critical for ion selectivity and transport. J Biol Chem, vol. 275, No. 31, pp. 23927-23932.*
Vamvakopoulos NC et al (1977) The effect of magnesium and manganese ions on the structure and template activity for reverse transcriptase of polyribocytidylate and its 2'-o-methyl derivative. Nucleic Acid Res, vol. 4, No. 10, pp. 3589-3597.*
Supek F et al (May 1996) A yeast manganese transporter related to the macrophage protein involved in conferring resistance to mycobacteria. Proc. Nat. Acad. Sci., USA, vol. 93, pp. 5105-5110.*
Aussel C et al (1996) Submicromolar La3+ concentrations block the calcium release-activated channel, and impair CD69 and CD25 expression in CD3- or thapsigargin-activated Jurkat cells. Biochem J, vol. 313, pp. 909-913.*
Poulsen J-C et al (1995) Thapsigargin-sensitive Ca2+-ATPases account for Ca2+ uptake to inositol 1,4,5-trisphosphate-sensitive and caffeine-sensitive Ca2+ stores in adrenal chromaffin cells. Biochem J, vol. 307, pp. 749-758.*
Van Baelen K et al (2004) The Ca2+/Mn2+ pumps in the golgi apparatus. Biochim et Biophys Acta, vol. 1742, pp. 103-112.*
Weed RI et al (1960) The uptake of divalent manganese ion by mature normal human red blood cells. J General Physiol, vol. 44, pp. 301-314.*
Lennerstrand J et al (Jun. 2007) Biochemical studies on the mechanism of human immunodeficiency virus type 1 reverse transcriptase resistance to 1-(beta-D-dioxolane) thymine triphosphate. Antimicrob Agents Chemother, vol. 51, No. 6, pp. 2078- 2084.*
Montaner LJ et al (1994) Interleukin-10 inhibits initial reverse transcription of human immunodeficiency virus type 1 and mediates a virostatic latent state in primary blood-derived human macrophages in vitro. J Gen Virol, vol. 75, pp. 3393-3400.*
Simm M et al (Nov. 8, 1996) Synthesis of full-length viral DNA in CD4-positive membrane vesicles exposed to HIV-1. J Biol Chem, vol. 271, No. 45, pp. 28266-28270.*
Nissley DV et al (Nov. 1998) Hybrid Ty1/HIV-1 elements used to detect inhibitors and monitor the activity of HIV-1 reverse transcriptase. PNAS, vol. 95, pp. 13905-13910.*
Okorokov et al. Energy-Dependent Transport of Manganese Into Yeast Cells and Distribution of Accumulated Ions; European Journal of Biochemistry, vol. 75 (1977) pp. 373-377.*
Bates et al. Candida Albicans PMR1P, A Secretory Pathway P-Type Calcium/Manganese Atpase, is Required for Glycosylation and Virulence; The Journal of Biological Chemistry, vol. 280, No. 24 (2005) pp. 23408-23415.*
Ash and Schramm, "Determination of Free and Bound Manganese(II) in Hepatocytes from Fed and Fasted Rats", *J. Biol. Chem.*, vol. 257, No. 16, pp. 9261-9264, 1982.
Beeler, Troy et al., "Regulation of cellular $Mg^{2+}$ by *Saccharomyces cerevisiae*", *Biochimica et Biophysica Acta*, 1323, pp. 310-318, 1997.
Bock, Charles W. et al., "Manganese as a Replacement for Magnesium and Zinc: Functional Comparison of the Divalent Ions", *J. Am. Chem. Soc.*, vol. 121, pp. 7360-7372, 1999. (Supporting information included, 121 pages.).
Boeke, Jef. D. et al., "Ty Elements Transpose through an RNA Intermediate", *Cell*, vol. 40, pp. 491-500, 1985.
Boeke, Jef. D. et al., "A positive selection for mutants lacking orotidine-5'-phosphate decarboxylase activity in yeast: 5-fluoro-orotic acid resistance", *Mol. Gen. Genet.*, vol. 197, pp. 345-346, 1984.

(Continued)

*Primary Examiner*—Jon P Weber
*Assistant Examiner*—Paul C. Martin
(74) *Attorney, Agent, or Firm*—DLA Piper LLP (US)

(57) ABSTRACT

Methods of identifying agents that modulate reverse transcriptase activity in a cell by affecting manganese ion transport across a membrane of the cell are provided, as are agents identified using such methods. Also provided are methods of modulating reverse transcriptase activity by affecting manganese ion concentration. In addition, methods of reducing or inhibiting infection of cells with a retrotransposable element are provided.

16 Claims, 5 Drawing Sheets

OTHER PUBLICATIONS

Curcio and Garfinkel, "Single-step selectionf or Ty*1* element retrotransposition" *Proc. Natl. Acad. Sci., USA,* vol. 88, pp. 936-940, 1991.

De Kruif, John de et al., "Biosynthetically lipid-modified human scFv fragments from phage display libraries as targeting molecules for immunoliposomes", *FEBS Letters,* vol. 399, pp. 232-236, 1996.

Ding. Y. et al., "Synthesis and Biological Activity of Oligosaccharide Libraries", *Adv. Expt. Med. Biol.,* vol. 376, pp. 261-269, 1995.

Filler and Lever, "Effects of Cation Substitutions on Reverse Transcriptase and on Human Immunodeficiency Virus Production", *AIDS Res. Hum. Retroviruses,* vol. 13, No. 4, pp. 291-299, 1997.

Garfinkel, David. R. et al., "Ty Element Transposition: Reverse Transcriptase and Virus-like Particles", *Cell,* vol. 42, pp. 507-517, 1985.

Gold, Larry et al., "Diversity of Oligonucleotide Functions", *Ann. Rev. Biochem,* vol. 64, pp. 763-797, 1995.

Goldstein, Alan L. et al., "Three New Dominant Drug Resistance Cassettes for Gene Disruption in *Saccharomyces cerevisiae*", *Yeast,* vol. 15, pp. 1541-1553, 1999.

Gordon, Eric M., "Applications of Combinatorial Technologies to Drug Deiscovery", *J. Med. Chem.,* vol. 37, No. 10, pp. 1385-1401, 1994.

Karaoghu, Denise et al., "Funcitonal Characterization of Ost3p. Loss of the 34-kD Subunit of the *Saccharomyces cerevisiae* Oligosaccharyltransferase Results in Biased Underglycosylation of Acceptor Substrates", *J. Cell Biol.,* vol. 130, No. 3, pp. 567-577, 1995.

Lawler, Joseph F. et al., "Frameshift Signal Transplantation and the Unambiguous Analysis of Mutations in the Yeast retrotransposon Ty1 Gag-Pol Overlap Region", *J. Virol.,* vol. 75, No. 15, pp. 6769-6755, 2001.

LeGrice, Stuart F.J. et al., "Purification and Characterization of Human Immunodeficiency Virus Type 1 Reverse Transcriptase", *Meth. Enzymol.,* vol. 262, pp. 130-144, 1995.

Liang, Rui et al., "Parallel Synthesis and Screening of a Solid Phase Carbohydrate Library", *Science,* vol. 274, pp. 1520-1522, 1996.

Mandal, Sebjani et al., "Manganese Selectivity of Pmr1, the Yeast Secretory Pathyway Ion Pump, Is Definted by Residue Gln$^{783}$ in Transmembrane Segment 6", *J. Biol. Chem.,* vol. 275, pp. 23933-23938, 2000.

Mellor, Jane et al., "Reverse transcriptase activity and Ty RNA are associated with virus-like particles in yeast", *Nature,* 318, pp. 583-586, 1985.

Sikorski and Hieter, "A System of Shuttle Vectors and Yeast Host Strains Designed for Efficient Manipulation of DNA in *Saccharomyces cerevisiae*", *Genetics,* vol. 122, pp. 19-27, 1989.

Steitz, Thomas A., "DNA Polymerases: Structural Diversity and Common Mechanisms", *J. Biol. Chem.,* vol. 274, No. 25, pp. 17394-17398, 1999.

Wei, Li-Na et al., "Receptor-interacting Protein 140 Directly Recruits Histone Deacetylases for Gene Silencing", *J. Biol. Chem.,* vol. 275, No. 52, pp. 40782-40787, 2000.

Wilhelm, Marcelle et al., "Expression of an active form of recombinant Ty1 reverse transcriptase in *Escherichia coli*: a fusion protein containing the C-terminal region of the Ty1 integrase linked to the reverse transcriptase-RNase H domain exhibits polymerase and RNase H activities", *Biochem J.,* vol. 38, pp. 337-342, 2000.

Xu and Boeke, "Host genes that influence transposition in yeast: The abundance of a rare tRNA regulates Ty1 transposition frequency", *Proc. Natl. Acad. Sci.,* vol. 87, pp. 8360-8364, 1990.

York, William S., "The structures of arabinoxyloglucans produced by solanaceous plants", *Carb. Res.,* vol. 285, pp. 99-128, 1996.

\* cited by examiner

MANGANESE ION REGULATION OF REVERSE TRANSCRIPTASE ACTIVITY AND METHODS OF MODULATING SAME

This application claims the benefit of priority under 35 U.S.C. §365 of PCT/US03/07879 filed Mar. 12, 2003 and under 35 U.S.C. § 119(e)(1) of U.S. Ser. No. 60/363,708, filed Mar. 12, 2002, the entire content of which is incorporated herein by reference.

This invention was made in part with government support under Grant No. GM 36481 awarded by the National Institutes of Health. The United States government has certain rights in this invention.

BACKGROUND OF THE INVENTION

1. Field of the Invention

The invention relates generally to methods of manipulating manganese levels to alter reverse transcriptase activity, and more specifically to methods of identifying agents that modulate reverse transcriptase activity, to agents identified using such methods, and to methods of using such agents to modulate reverse transcriptase activity, for example, in a cell.

2. Background Information

Viral infection and replication in host cells is associated with various diseases in plants and animals. Retroviruses, for example, are a type of virus that associated with various cancer and with human immunodeficiency virus (HIV), which is responsible for AIDS in humans. As such, the morbidity and mortality associated with viral infections and the disease associated with such infections causes great suffering and further results in a great economic burden on individuals and society.

HIV was identified as the causative agent of AIDS in 1983 and, AIDS has progressed to being one of the greatest health problems in the world, with medical and social consequences likely to extend long into the future. The World Health Organization has estimated that between eight and ten million people are currently infected with HIV, and that approximately ten times as many individuals will be affected in the next decade. Further, the large pool of HIV carriers and the failure of HIV infection to cause early and easily identified symptoms makes the development of effective antiviral treatments a medical priority.

Retroviruses such as HIV replicate through an RNA intermediate as part of their life cycle. All retroviruses encode proteins that are required for their replication and transmission, including, for example, an integrase that allows the virus to integrate into the genomic DNA of an infected cell, and a reverse transcriptase that is involved in replication of the retrovirus genome. The activities of these retroviral proteins, including the reverse transcriptase, are central to the replication of retroviruses and, therefore, have been the target of drugs to treat retroviral infection, including HIV infection. Reverse transcriptase inhibitors are the current treatment of choice for AIDS patients. However, retroviral therapy, as for other viral therapies, are commonly of limited effectiveness due to development of viral resistance to the drug.

In an effort to overcome problems associated with the development of resistance to a single drug, "cocktails" containing a combination of drugs have been used, and have been shown to be effective for longer periods of time. Unfortunately, drugs that are effective in inhibiting the activity of retroviral proteins often inhibit normal proteins involved in survival and proliferation of the retroviral infected cells, thus causing undesirable and often severe side effects. Thus, a need exists for developing agents and methods for more effectively and specifically inhibiting retroviral enzymes without substantially affecting normal cellular enzymes. The present invention satisfies this need provides additional advantages.

SUMMARY OF THE INVENTION

The present invention relates to a method of identifying an agent that modulates reverse transcriptase activity in a cell. In one embodiment, a method of the invention can be performed, for example, contacting a cell membrane, which contains a divalent cation transporting protein that transports manganese ions, and can transport other divalent cations, with a test agent; and detecting altered manganese ion transport due to contact with the test agent as compared to manganese ion transport in the absence of the test agent. The cell membrane contacted with the test agent can be an isolated cell membrane, which contains the divalent cation transporting protein, for example, a eukaryotic cell membrane such as a yeast cell membrane or a mammalian cell membrane (e.g., a human cell membrane), and can be any cell membrane of a cell, including, for example, the cell surface membrane, or a cell membrane of associated with the Golgi apparatus, mitochondria, endoplasmic reticulum, or nucleus.

Generally, an isolated cell membrane useful in a method of the invention delimits at least a first compartment and a second compartment, wherein the divalent cation transporting protein in the membrane can transport divalent cations, including manganese, from the first compartment to the second, or from the second compartment to the first; or can transport divalent cations into and out of both compartments, including transporting manganese into and/or out of at least one compartment. For example, a portion of a cell membrane can be obtained using a microcapillary, wherein the cell membrane can separate the contents of the microcapillary (i.e., a first compartment) from a medium in which the microcapillary is contacted (i.e., a second compartment). According to such an example, the test agent can present in the medium (second compartment), manganese ions can be present in the first and/or second compartment, and altered manganese ion transport can be detected by examining the first compartment or the second compartment or both.

The cell membrane contacted with the test agent also can be a cell membrane in situ, in which case the method is performed by contacting a cell, which comprises the cell membrane. The cell can be any type of cell that contains a cell membrane with a divalent cation transporting protein and that supports reverse transcriptase activity. As such, the cell can be a eukaryotic cell, including, for example, an insect cell (e.g., a *Drosophila* cell), a fungus cell (e.g., a *Neurospora* cell), a yeast cell, a *C. elegans* cell, an amphibian cell (e.g., sea urchin), an avian cell (e.g., a chick embryo fibroblast), or a human cell (e.g., a human T lymphocyte). Further, such cells useful in a method of the invention can be cells of a cell line, which have been adapted to culture; can be cells of a primary cell culture, which can be maintained in culture for at least a short period of time; or cells that have been isolated from a living organism, for example, cells isolated from a human subject.

The divalent cation transporting protein of the cell membrane can be any transporter that allows the selective passage of manganese ions across the cell membrane. The transporter generally is an active transporter that normally functions to pump manganese ions into a cell, out of a cell, or in either direction depending, for example, on the relative concentration of manganese ions in one of the compartments, particularly an intracellular compartment, as compared to a manganese concentration typically found in the compartment in an otherwise normal cell. For example, the divalent cation transporting protein can be a P-type ATPase, for example, a *Saccharomyces cerevisiae* Pmr1p protein, which is a calcium ion and manganese ion transporting protein, or a homolog thereof, including for example, isoforms of the human ATP-dependent calcium ion pump, PMR1 (ATPase 2C1); the Pmr1p homologs ATP2 µl and ATP2A2, which are expressed in cardiac cells; and ATP2A3, which is expressed ubiquitously.

An agent that modulates reverse transcriptase activity, as identified according to a method of the invention, can be one that alters the transport of all cations that are transported by the divalent cation transporting protein, or, in particular, an agent that only alters manganese ion transport, but not any other divalent cations (if any) that can be transported by the divalent cation transporting protein. Further, the method can be used to identify an agent that reduces or inhibits manganese ion transport out of a cell, or that increases manganese transport into a cell, thus providing an agent that can increase an intracellular manganese ion concentration in a cell above a level normally found in the cell; or the method can be used to identify an agent that reduces or inhibits manganese ion transport into a cell, or that increase manganese ion transport out of a cell, thus providing an agent that can decrease an intracellular manganese ion concentration in a cell below a level normally found in the cell.

Altered manganese ion transport can be detected using any of various methods useful for detecting the presence or absence, or the concentration or relative amount of manganese ion, in a compartment, including in vivo (i.e., in a cell) in an intracellular compartment, or in vitro (i.e., using an isolated cell membrane) in a compartment delimited by the cell membrane. As such, manganese ion concentration in one (or more) compartments can be measured using a chemical or physical means, for example, using a polarographic (voltametric) method or a radiometric method. In addition, or alternatively, as disclosed herein, altered manganese ion transport can be detected by detecting altered reverse transcriptase activity in a relevant compartment, which can be in intracellular compartment or other compartment delimited by the cell membrane. Reverse transcriptase activity can be measured using a polyribonucleotide template, or a polydeoxyribonucleotide template, or both. Further, the reverse transcriptase activity being detected can be that of a reverse transcriptase that is present in a cell due, for example, to infection of the cell by a retrotransposon that expresses the reverse transcriptase, or to expression in a cell of an exogenously added nucleic acid molecule encoding the reverse transcriptase, or can be that of an isolated reverse transcriptase polypeptide.

In another embodiment, a method of identifying an agent that modulates reverse transcriptase activity in a cell can be performed, for example, by contacting a cell expressing a reverse transcriptase with a test agent; and detecting altered reverse transcriptase activity due to contact with the test agent as compared to reverse transcriptase activity in the absence of the test agent, wherein the test agent alters manganese ion concentration in the cell. A test agent useful in a method of the invention can be any agent suspected of having the ability to alter manganese ion transport across a cell membrane, including any agent suspected of having the ability to alter the activity of a divalent cation transporting protein. As such, the test agent can be a peptide, a polynucleotide, a small organic molecule, a peptidomimetic, or the like.

Altered reverse transcriptase activity due to contact with a test agent comprises measuring cDNA produced by the reverse transcriptase using a polynucleotide template in the cell. The polynucleotide template can be a polydeoxyribonucleotide template or a polyribonucleotide template. In one embodiment, the polynucleotide template comprises a nucleotide sequence of a retrotransposable element, for example, a nucleotide sequence of a retrotransposon such as a Ty retrotransposon (e.g., a Ty-1 element); or a nucleotide sequence of a retrovirus such as a human immunodeficiency virus (HIV; e.g., HIV-1) or an avian myeloblastosis virus. In another embodiment, the reverse transcriptase is a reverse transcriptase expressed in a cell from a retrotransposable element present in the cell, for example, a Ty-1 element or a retrovirus such as HIV-1.

The cell contacted with the agent can be any cell as disclosed herein, for example, a yeast cell (e.g., a *S. cerevisiae* cell), an avian cell (e.g., a chick embryo fibroblast), or a human or other mammalian cell (e.g., a T lymphocyte), including cells isolated from a subject. Further, the cell can be one of a plurality of cells, which can be the same or different or a combination of some that are the same and some that are different, wherein, preferably, cells of the plurality are substantially isolated from each other. As such, the methods of the invention can be adapted so as to be performed in a high throughput format. In one embodiment, each of the cells of the plurality is arranged in an array, which can be an addressable array, for example, on a solid support such as a microchip, on a glass slide, on a bead, or in a well. In another embodiment, each of the cells of the plurality is contacted with a test agent, which, in various aspects, can include contacting two or more cells of the plurality that are the same with the same test agent (thus providing duplicates, triplicates, etc., screened in parallel) or with different test agents (thus providing a means to examine a variety of different test agents, e.g., each test agent of a library of random, biased or variegated test agents); or can include contacting two or more cells of the plurality that are different with the same test agent (thus providing a means to determine the effect of a test agent on different cells or cell types) or with different test agents (thus providing a means to examine the effect of a variety of different test agents on a variety of different cells); or can include various combinations of the above described aspects. Accordingly, the present invention also provides an agent that modulates reverse transcriptase activity in a cell, such an agent being identified according to a method as disclosed herein.

The present invention also relates to a method of modulating reverse transcriptase activity in a cell. Such a method can be performed, for example, by contacting the cell with an agent that alters manganese ion transport across a cell membrane of the cell, thereby modulating reverse transcriptase activity in the cell. The agent can be one that reduces or inhibits manganese ion transport out of the cell. In one aspect, the agent is one that reduces or inhibits manganese ion transport across a cell membrane of the cell, but that does not alter the transport of other divalent cations across the cell membrane. In another aspect, the agent is one alters the activity of a divalent cation transporting protein in a cell membrane of the cell, for example, a P-type ATPase such as a Pmr1p protein or a homolog thereof.

The present invention further relates to a method of modulating reverse transcriptase activity by contacting the reverse transcriptase, under conditions suitable for reverse transcriptase activity, with a predetermined concentration of manganese ions. The conditions can be any conditions suitable for reverse transcriptase activity, including, for example, an in vitro reaction mixture containing a buffer, deoxyribonucleotide triphosphates, and/or a primer, and/or can include an extract of a cell, for example, an extract of a cell infected with a retrovirus. In one aspect, the method further includes contacting the reverse transcriptase with a predetermined concentration of magnesium ions. As such, the method provides a means to modulate the relative activity of a reverse transcriptase with respect to a polyribonucleotide template as compared to a polydeoxyribonucleotide template.

The present invention also relates to a method of ameliorating a retrovirus infection in a subject. Such a method can be performed, for example, by contacting cells of the subject with an agent that alters manganese ion transport in a retrovirus infected cell of the subject. The cells can be contacted with the agent in vivo, for example, by administering the agent systemically to the subject such that the agent circulates to the retrovirus infected cells, or by administering the agent at or near the site of the retrovirus infected cells in the subject. Alternatively, the cells can be contacted with the agent ex vivo, after which the cells can be expanded in culture without concern for replication of the retrovirus due to inhibition of the retrovirus reverse transcriptase, and uninfected cells of the expanded population can be selected and administered back into the subject. Preferably, the agent is one that reduces or inhibits a divalent cation transporting protein activity in the retrovirus infected cell, and more preferably, the agent does not alter transport of a divalent cation other than a manganese ion by the divalent cation transporting protein. As such, a method of the invention can be useful, for example, for treating a human infected with HIV-1, or for treating poultry infected with avian myeloblastosis virus, and can further be useful, for example, for treating cats infected with feline leukemia virus, and the like.

The present invention further relates to a high throughput assay for identifying an agent that alters manganese ion transport by a divalent cation transporting protein in a cell. Such a method can be performed, for example, by providing an array, which can be an addressable array, containing a plurality of cells, including one or more cells at positions of the array, that express a heterologous divalent cation transporting protein, wherein the heterologous divalent cation transporting protein transports at least manganese ion. For example, the plurality of cells can be a plurality of yeast cells, insect cells, avian cell, mammalian cells, or combinations thereof. The heterologous divalent cation transporting protein can be any transporter that is heterologous with respect to the cell containing the transporter (i.e., any transporter that is not expressed in the particular cell in nature, or that is expressed from a recombinant nucleic acid molecule introduced into the cell). In one embodiment, the cell is a yeast cell, and the heterologous transporter is a human divalent cation transporting protein expressed in the yeast cell. In one aspect of this embodiment, the human divalent cation transporting protein comprises a human Pmrp1 transporting protein.

A support comprising the array can be any support suitable for containing cells of the plurality being contacted with an agent (or otherwise in the array) in relative isolation from other cells of the plurality. For example, the support can be a microchip, wherein cells of the plurality can be positioned on the surface of the microchip, including, for example, in a depression or other delimited area of the microchip. The support also can comprise an array of wells, for example, as provided in a microtiter plate or the like, which can contain 8 wells, 24 wells, 96 wells, 384 wells, 1092 wells, or any number of wells as desired, and can be composed of any suitable material that is not toxic to the cells to be contacted with the wells and that does not substantially react with reagents to be contacted with the cells in the well, including, for example, test agents to be added to the wells.

The cells of the plurality can further express a reporter gene, particularly wherein expression of the reporter gene is regulated directly or indirectly by manganese ion concentration in the cell. In one embodiment, the reporter gene is a gene regulated by reverse transcriptase activity in the cell. In one aspect of this embodiment, the reporter gene comprises a retrotransposable element, wherein expression of the reporter gene comprises detecting integration (or a lack thereof) of the element into the genome of the cell. In another embodiment, the reporter gene comprises is a hybrid Ty-HIV (HART) reporter construct, which is useful for detecting reverse transcriptase activity.

The present invention also relates to a method of identifying an agent that modulates reverse transcriptase activity in a cell. Such a method can be performed, for example, by contacting cells of an array of cells with at least one test agent, wherein the cells comprise a divalent cation transporting protein, which transports manganese ions; and detecting altered manganese ion transport in cells of the array due to contact with the test agent as compared to manganese ion transport in the absence of the test agent, thereby identifying an agent that modulates reverse transcriptase activity in a cell. The cells of the array can be eukaryotic cells, for example, yeast cells or mammalian cells. Further, the divalent cation transporting protein expressed by the cells of the array can be an endogenous transporter, or can be a heterologous divalent cation transporting protein. In one embodiment, the method is performed using an array of yeast cells. In one aspect of this embodiment, the heterologous divalent cation transporting protein comprises a human divalent cation transporting protein. In another aspect of this embodiment, the heterologous divalent cation transporting protein comprises a human Pmrp1 transporting protein.

BRIEF DESCRIPTION OF THE DRAWINGS

FIG. 3A shows the VLP-associated RT activity in 10 mM $MgCl_2$ for the indicated gradient fractions. RT activity of VLPs isolated from wild-type (PMR1) cells (black circles with solid black line) and pmr1Δ cells (gray circles with dashed gray line). RT activity of wild-type VLPs was adjusted to normalize for slight differences in the amount of RT protein.

FIG. 3B shows the $Mg^{2+}$-dependent (circles) and $Mn^{2+}$-dependent (triangles) RT activity of VLPs isolated from wild-type cells (solid black lines) and pmr1Δ cells (dashed gray lines). 100% incorporation corresponds to 2 pmol dGTP incorporated/μl of VLPs (fraction 24).

FIG. 4A shows metal ion competition for Ty1 VLPs.

FIG. 4B shows metal ion competition for hetero-dimeric HIV-1.

FIG. 4C shows metal ion competition for wild-type Ty1 RT.

FIG. 4D shows wild-type (black) compared to D211N (red) Ty1 RT.

FIG. 5E shows the activity of wild-type RT (black) and D211N RT (red) for $MgCl_2$ (squares) and $MnCl_2$ (diamonds) represented on a Hill plot. Under the experimental conditions, more than 94% of the divalent cation concentration was free, consistent with the Hill equation (i.e., $\log(v/(V_{Max}-v))= n_H\log\{M\}+\log K_{0.5}$; where v=velocity, $V_{Max}$=maximal velocity, $n_H$=Hill coefficient, $\{M\}$=divalent cation concentration, and $K_{0.5}$=macroscopic equilibrium constant for the divalent cation). Solid lines correspond to results of linear regression analysis of each data set. Slopes of these lines are given as Hill coefficients in Table 1.

DETAILED DESCRIPTION OF THE INVENTION

Figure 1:
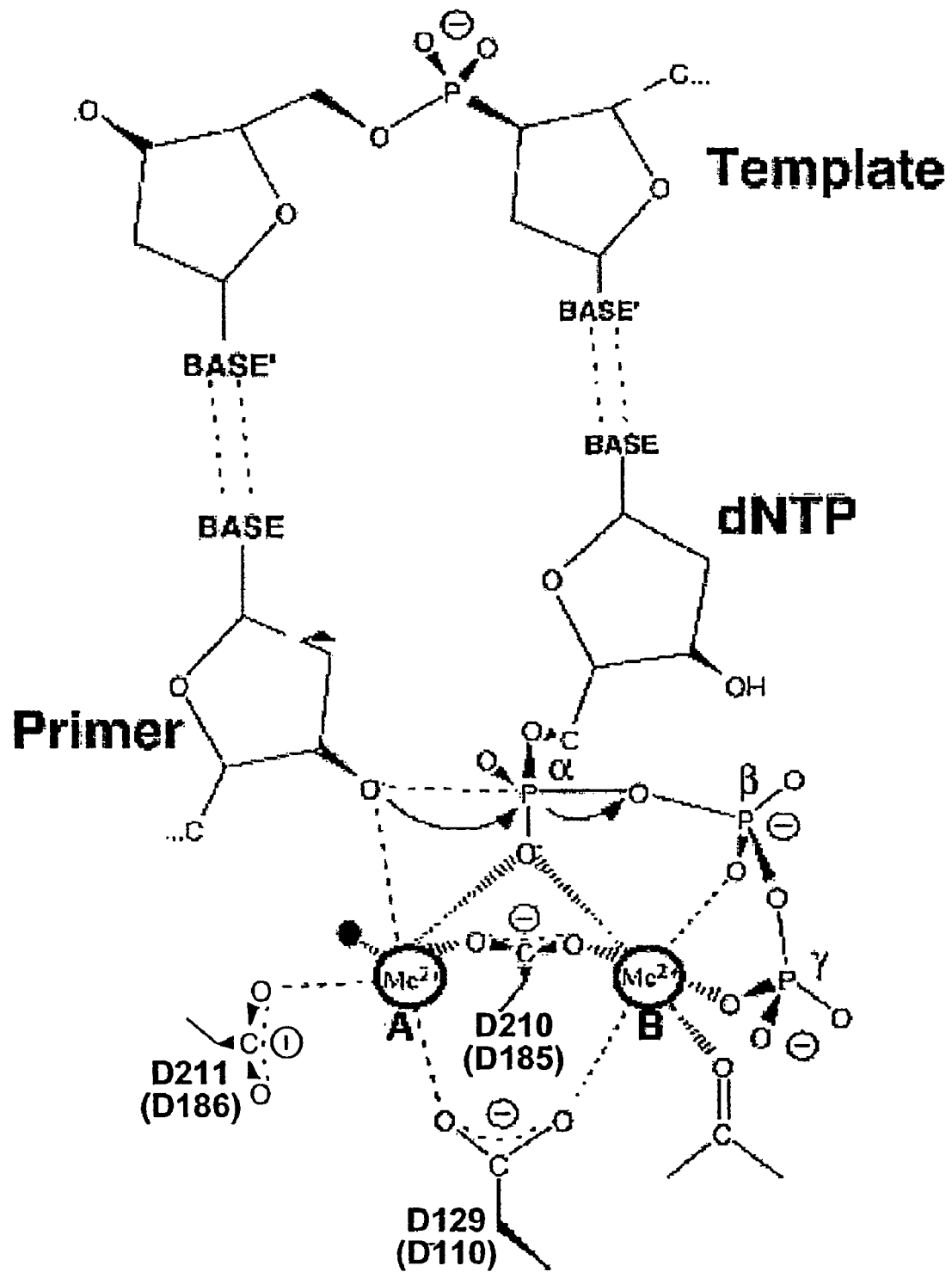
FIG. 1 illustrates a proposed two metal ion mechanism of DNA polymerization for Ty1/HIV-1 reverse transcriptase (RT) based on the crystal structures of mammalian DNA polymerase β (Pelletier et al., Science 264: 1891-1903, 1994; Sawaya, Science 264: 1930-1935, 1994; Sawaya et al., Biochemistry 36: 11205-11215, 1997), Taq DNA polymerase (Li et al., EMBO J. 17: 7514-7525, 1998), T7 DNA polymerase (Doublie et al., Nature 391, 251-8, 1998), and HIV-1 RT (Huang et al., Science 282, 1669-1675, 1998)—modified from Brautigam and Steitz, Curr. Opin. Struct. Biol. 8: 54-63, 1998. Aspartic acid-129 (D129) and D210 for Ty1, and D110 and D185 for HUV-1, represent the two active site aspartates that are conserved among DNA polymerases, while D211 for Ty1 and D186 represent the third active site aspartate that is conserved among reverse transcriptases.

The present invention provides methods for identifying an agent that modulates the activity of reverse transcriptase. The methods of the invention are based on the demonstrated ability of the concentrations of certain divalent cations to affect the activity of reverse transcriptase in a cell. The validity of a method of the invention is exemplified by the identification of functional mutations to a divalent cation transporting protein that is localized within a membrane of a yeast cell and is responsible for the regulation of intracellular divalent cation concentrations. Specifically, mutations to a transporting protein that resulted in altered transport of divalent cation, manganese ion, significantly modulated reverse transcriptase activity. Accordingly, the present invention provides methods of identifying an agent that modulates reverse transcriptase activity, and further provides methods of modulating reverse transcriptase activity, and methods of ameliorating a retrovirus infection in a subject.

Reverse transcriptase (RT) is an enzyme that can construct double stranded DNA molecules from a single stranded polynucleotide template, such as the RNA template of a retrovirus genome. Although originally discovered in retroviruses, RT is encoded by the genomes of a wide variety of retrotransposable elements including, for example, retrotransposons such as Ty elements. All known RTs are multifunctional, having three different enzymatic activities: an RNA-dependent DNA polymerase activity, an RNase H activity, and a DNA-dependent DNA polymerase activity. During retroviral replication RNA-dependent DNA polymerase activity generates a DNA strand (the minus strand) complementary to the viral RNA. This step is followed by the degradation of the original viral RNA strand by RNase H, then the DNA-dependent DNA polymerase activity generates a second DNA strand (the plus strand) complementary to the first. The double stranded DNA is integrated into the host genome through the action of the retroviral integrase, resulting in a latent infection of the host cell.

The term "retrotransposable element" is used broadly herein to refer to retrotransposons and retroviruses, which are characterized, in part, in that they encode a RT and an integrase, can integrate into a host cell genome, and can be maintained in the host cell in a latent form. Retrotransposons are exemplified by copia elements of *Drosophila* and Ty elements of *Saccharomyces cerevisiae*. Retrotransposition of a Ty element is a replicative process involving reverse transcription of Ty mRNA and integration of Ty cDNA into the genome. *Saccharomyces cerevisiae* harbors five types of Ty elements, all of which are long terminal repeat (LTR) retrotransposons, including Ty1, which numbers approximately 30 copies per haploid genome. Transcription of Ty1 produces a terminally redundant RNA molecule from which the structural protein, Gag, and enzymes, Pol, are translated. Specifically, GAG encodes the capsid (CA) protein and POL encodes the protease (PR), integrase (IN), and reverse transcriptase/RNase H (RT) (Boeke et al., *Cell* 40: 491-500, 1985; Garfinkel et al., *Cell* 42: 507-517, 1985; Mellor et al., *Nature* 318: 583-586, 1985). The Ty1 life cycle can be divided into three phases: 1) expression and assembly, 2) reverse transcription, 3) integration. Gag and Gag-Pol proteins are translated and co-assembled with Ty1 RNA in the cytoplasm, forming virus-like particles (VLPs). VLPs are direct transposition intermediates in which reverse transcription occurs (Eichinger and Boeke, *Cell* 54: 955-966, 1988; Garfinkel et al., *J. Virol.* 65: 4573-4581, 1991). Reverse transcription of Ty1, like that of retroviruses, involves conversion of the terminally redundant RNA into a double-stranded DNA copy. During this process, the RT uses both RNA and DNA as templates for DNA synthesis. RT activity requires primer, template, and deoxynucleotide triphosphates (dNTPs) as well as a divalent cation, magnesium ion or manganese ion (Wilhelm et al., *Biochem. J.* 348: 337-42, 2000, which is incorporated herein by reference; Garfinkel et al., supra, 1985). The contents of the DNA-containing VLPs are transported to the nucleus, where integration into host DNA occurs (Kenna et al., *Mol. Cell. Biol.* 18: 1115-1124, 1998; Moore et al., *Mol. Cell. Biol.* 18: 1105-1114, 1998).

Retroviruses, which can infect fish, amphibian, reptile, bird, and mammalian cells, including, for example, human immunodeficiency virus (HIV), which infects human T lymphocytes, are classified as oncoviruses such as avian leukemia virus (ALV), Rous sarcoma virus (RSV), Mason-Pfizer monkey virus, and simian retrovirus type 1 and type 2; lentiviruses such as human immunodeficiency virus type I (HIV-1) and type II (HIV-2); and spumaviruses. In addition to causing disease, retroviruses have been used as a basis for designing vectors for gene therapy. As discussed above, retroviruses have a two stage life cycle, existing in an RNA form and a DNA form. The RNA form of the virus is packaged into an infectious particle that is coated with a glycoprotein (env), which is recognized by receptors on the host cell. This interaction promotes a receptor mediated internalization event, resulting in exceptionally efficient delivery of the retroviral genome into the cell, where it is converted into a DNA form and can integrate into the host cell genome.

Reverse transcriptase (RT) activity requires, in addition to the RT, a primer, a template, and deoxynucleotide triphosphates (dNTPs), as well as a divalent cation, for example, magnesium or manganese (Garfinkel et al., supra, 1985; Wilhelm et al., supra, 2000). Sequence and structural comparisons among reverse transcriptase and DNA polymerases strongly favor a nucleotidyl transfer reaction mechanism activated by two divalent cations sharing a common ligand, as originally found for 3'-5'-exonuclease reactions (Beese and Steitz, *EMBO J.* 10: 25-33, 1991; Han et al., *Biochemistry* 30: 11104-11108, 1991; see, also, FIG. 1). Crystal structures of mammalian DNA polymerase β (pol β; Pelletier et al., *Science* 264: 1891-1903, 1994; Sawaya et al., *Biochemistry* 36: 11205-11215, 1997), *Thermus aquaticus* (Taq) DNA polymerase (Li et al., *EMBO J.* 17: 7514-7525, 1998), T7 DNA polymerase (Doublie et al., *Nature* 391: 251-258, 1998) and HIV-1 RT (Huang et al., *Science* 282: 1669-1675, 1998) in primer-template complex with dNTP (the ternary complex) revealed that all of the polymerases bind two divalent cations (normally magnesium ions) in a binuclear complex at the active site. In the homologous palm domains, the two metal ions share two completely conserved aspartate 5 ligands (see FIG. 1; metals A and B). In the ternary complexes, metal ion A is proposed to facilitate the attack of the 3' hydroxyl of the primer terminus on the α-phosphorus of the dNTP (Doublie et al., supra, 1998; Steitz, *J. Biol. Chem.* 274: 17395-17398, 1999). Both metal ions are hypothesized to stabilize the pentacovalent transition state, while metal ion B is proposed to facilitate the leaving of pyrophosphate (Id). However, among RTs, a third conserved aspartate residue (see FIG. 1) has been positioned at the active sites of HIV-1 RT structurally (Huang et al., *Science* 282: 1669-1675, 1998) and Ty1 RT functionally (Uzun and Gabriel, *J. Virol.* 75: 6337-6347, 2001, which is incorporated herein by reference).

As disclosed herein, manipulation of manganese ions in a cell can modulate RT activity, including reducing or inhibiting RT activity. As used herein, the term "reverse transcriptase activity" refers to the polymerase and/or RNAase H activity of a RT, including the ability to effect the formation of a polydeoxyribonucleotide sequence using an RNA template or a DNA template, and/or the ability to degrade an RNA component of a DNA/RNA hybrid. RT activity can be measured using any assay as disclosed herein or otherwise known in the art. For example, RT activity can be measured in a yeast cell based assay using a Ty-HIV-1 (HART) reporter construct, which includes domains of TY-1, His3AI and the RT/RNAse H domain of human HIV-1 (Nissley et al., *Nature* 380: 30, 1996; Nissley et al., *Proc. Natl. Acad. Sci., USA* 95: 13905-13910, 1998, each of which is incorporated herein by reference).

The term "modulate", when used in reference to RT activity, means that the RT activity is increased, or is reduced or inhibited, as compared to a control level. Generally, the control level is the RT activity under defined conditions in the absence of contact with an ant that alters manganese ion transport. The terms "reduce or inhibit" are used together herein because it is recognized that, depending on a particular assay being used, the level of RT activity can be reduced below a level that can be detected using the assay and, therefore, it may not always be clear whether the RT activity is completely inhibited. Similarly, the term "alter", when used in reference to manganese transport or to divalent cation transporting protein activity, means that the level of such transport or activity is increased, or is reduced or inhibited, with respect to a control level of activity. As such, the terms "modulate" and "alter" can be used interchangeably.

A method of the invention can be performed, for example, by contacting a cell membrane, which contains a divalent cation transporting protein that transports manganese ions, and can transport other divalent cations, with a test agent; and detecting altered manganese ion transport due to contact with the test agent as compared to manganese ion transport in the absence of the test agent. The term "cell membrane" is used broadly herein to refer to any membrane normally associated with a cell, particularly a eukaryotic cell. As such, a cell membrane useful in a method of the invention generally comprises a lipid bilayer and is exemplified by a cell surface membrane, which defines an intracellular compartment and an extracellular compartment, and by membranes associated with an organelle of a eukaryotic cell, for example, a nuclear membrane, Golgi apparatus membrane, mitochondrial membrane, and endoplasmic reticulum membrane.

The cell membrane contacted with the test agent can be an isolated cell membrane, which contains the divalent cation transporting protein, for example, a eukaryotic cell membrane such as a yeast cell membrane or a mammalian cell membrane (e.g., a human cell membrane), and can be any cell membrane of a cell, including, for example, the cell surface membrane, or a cell membrane of associated with the Golgi apparatus, mitochondria, endoplasmic reticulum, or nucleus. Alternatively, the cell membrane contacted with the test agent can be a cell membrane in situ, in which case the method is performed by contacting a cell, which comprises the cell membrane. The cell can be any type of cell that contains a cell membrane with a divalent cation transporting protein and that supports RT activity. As such, the cell can be a eukaryotic cell, including, for example, an insect cell (e.g., a *Drosophila* cell), a fungus cell (e.g., a *Neurospora* cell), a yeast cell, a *C. elegans* cell, an amphibian cell (e.g., sea urchin), an avian cell (e.g., a chick embryo fibroblast), or a human cell (e.g., a human T lymphocyte). Further, such cells useful in a method of the invention can be cells of a cell line, which have been adapted to culture; can be cells of a primary cell culture, which can be maintained in culture for at least a short period of time; or cells that have been isolated from a living organism, for example, cells isolated from a human subject.

A characteristic of a cell membrane useful in a method of the invention is that the it contains a divalent cation transporting protein. As used herein, the term "divalent cation transporting protein" or "divalent cation transporter" refers to a cell membrane-associated structure that is involved in the transport of divalent cations in one or both directions across the cell membrane. As such, it should be recognized that, for purposes of the present invention, a cell membrane generally is substantially impermeable to cations, particularly manganese and any other cation or cations that are transported by the particular divalent cation transporter being examined according to a screening method as disclosed herein. Divalent cation transporting proteins include ion channels, molecular transporters and ion pumps, and, in addition to manganese, divalent cations transported by such transporting proteins can include, for example, magnesium and calcium.

Ion channels are typically formed by the association of integral membrane proteins into structures having a central hydrophilic pore. Channel pores allow ions to equilibrate across membranes in response to their electrochemical gradients and at rates that are diffusion limited. Ion channels are characterized by their selectivity and gating properties. Selectivity refers to the rate at which different ion species pass through an open channel under standard conditions. Gating is the process that regulates the opening and closing of an ion channel. Thus, voltage-regulated ion channels respond to changes in membrane potential; ligand-regulated channels respond to the binding of particular ligands or intracellular messengers (e.g., cyclic nucleotides, calcium ions); and mechanosensitive channels respond to mechanical deformation (e.g., stretch).

Ion channels exist in resting (closed), open or inactivated (i.e., desensitized) states. Voltage-gated ion channels in the open state typically transition to an inactivated state, and must reacquire the ability to respond to an external stimulus during a recovery period. This may also be true of ligand-gated channels, particularly after prolonged exposure to an agonist. Certain channels are gated by more than one type of stimulus (e.g., an inward rectifying voltage-regulated potassium channel in cardiac muscle is activated by acetylcholine). Ion channels serve a variety of important cellular functions, including stimulation, excitability, signaling, excitation-secretion coupling, volume regulation and so on. Ion channels are implicated in a variety of pathophysiological disorders, including hypertension, cardiac arrhythmogenesis, non-insulin dependent diabetes mellitus, and seizures, and mediate the transmission of pain impulses by peripheral nerves (see, generally, Ackerman and Clapham, *New Engl. J. Med.* 336: 1575, 1997).

The ABC transporters comprise a superfamily that shares a highly conserved ATP-binding cassette (Higgins, *Ann. Rev. Cell Biol.* 8: 67-113, 1992). These transporters typically use ATP hydrolysis as a source of energy to pump diverse classes of molecules (e.g., sugars, peptides, inorganic ions, amino acids, oligopeptides, polysaccharides, proteins) across membranes against a concentration gradient. Each transporter is highly selective for a particular substrate and pumps unidirectionally. Some members of the ABC transporter family have ion channel activity. For example, the cystic fibrosis transmembrane regulator (CFTR), a cAMP and protein kinase A regulated chloride ion channel, uses ATP hydrolysis as a gating mechanism. P-glycoprotein (MDR) appears to be bifunctional, possessing drug transport as well as chloride channel activities; the latter is cell-volume regulated and requires the binding, but not the hydrolysis, of ATP. In both prokaryotes and eukaryotes, ABC transporters function in nutrient uptake, protein export and drug resistance (e.g., erythromycin resistance in *Staphylococcus*, daunomycin resistance in *Streptomyces*, chloroquine resistance in *Plasmodium*, and multidrug resistance in cancers).

Ion pumps are also involved in the active transport of ions across membranes. Ion pumps are members of the ion-transporting P-type ATPase family, which couple ion transport to a cycle of phosphorylation and dephosphorylation of an ATPase enzyme. In mammalian cells, this class includes the calcium ion ATPases, the sodium ion/potassium ion ATPases, and the hydrogen ion/potassium ion ATPases, the latter of which are involved in acid secretion in the stomach and are clinically important targets in peptic ulcer disease, gastroesophageal reflux disease (GERD) and gastric hyperacidity. The calcium ion ATPases and sodium ion/potassium ion ATPases, in comparison, are therapeutic targets in the treatment of heart failure.

A divalent cation transporting protein examined according to a method of the invention can be any transporter that is involved in the selective passage of manganese ions across the cell membrane. Such a transporter generally, but not necessarily, utilizes an active transport mechanism to pump manganese ions into a cell, out of a cell, or in either direction, depending, for example, on the relative concentration of manganese ions in one of the compartments, particularly an intracellular compartment, as compared to a manganese concentration typically found in the compartment in an otherwise normal cell. For example, the divalent cation transporting protein can be a P-type ATPase such as an *S. cerevisiae* Pmr1p protein, which is a calcium ion and manganese ion transporting protein, or a homolog thereof, including for example, a human calcium-transporting ATPase type 2C family member (ATP-dependent calcium ion pump, PMR1; e.g., ATPase 2C1; see GenBank Acc. Nos: AAF26295, AAF26296, and P98194; Hu et al., *Nat. Genet.* 24: 61-65, 2000; Sudbrak et al., *Hum. Mol. Genet.* 9: 1131-1140, 2000; Nagase et al., *DNA Res.* 7: 63-73, 2000; Stanchi et al., *Yeast* 18: 69-80, 2001, each of which is incorporated herein by reference) and isoforms thereof, as well as the Pmr1p homologs ATP2A1 and ATP2A2, which are expressed in cardiac cells, and ATP2A3, which is expressed ubiquitously, sequences of which can be obtained by a search, on the world wide web, at the URL "ncbi.nlm.nih.gov", in the Entrez Protein database.

Generally, an isolated cell membrane useful in a method of the invention delimits at least a first compartment and a second compartment, wherein the divalent cation transporting protein in the membrane can transport divalent cations, including manganese, from the first compartment to the second, or from the second compartment to the first; or can transport divalent cations into and out of both compartments, including transporting manganese into and/or out of at least one compartment. For example, a portion of a cell membrane can be obtained using a microcapillary, wherein the cell membrane can separate the contents of the microcapillary (i.e., a first compartment) from a medium in which the microcapillary is contacted (i.e., a second compartment). According to such an example, the test agent can be present in or added to the medium (second compartment), manganese ions can be present in the first and/or second compartment, and altered manganese ion transport can be detected by examining the first compartment or the second compartment or both.

Altered manganese ion transport can be detected using any method as disclosed herein or otherwise known in the art. For example, altered manganese ion transport can be detected by detecting movement of manganese ions from one compartment to another, by detecting a change in the concentration of manganese ions in one or both compartments, or by detecting a change in a functional activity associated with a change in manganese ion concentration in a compartment, for example, as disclosed herein, by detecting a change in RT activity in compartment. For example, altered manganese ion transport can be detected using a patch clamp method. The patch clamp technique is commonly used for examining transmembrane proteins, and can provide a "voltage clamp" measurement of ionic current in either a small "patch" of cell membrane, or the entire membrane of a small cell. Because the method measures current, it directly monitors the number of active channels in the membrane and, therefore, can be an appropriate assay for identifying agents that block or otherwise modulate divalent cation transporter activity (see, generally, Boulton et al. (eds.), Patch Clamp Applications and Protocols, Humana Press (1995); Neher and Sakmann (eds.), Single-Channel Recording, Plenum Press (1995), and DeFelice, Electrical Properties of Cells: Patch Clamp for Biologists (The Language of Science), Plenum Pub. Corp. (1997), each of which is specifically incorporated by reference in its entirety).

Altered magnesium ion transport also can be detected using a polarographic (voltametric) method or a radiometric method, in which the concentration of manganese ions can be determined.

Altered manganese ion transport due to contact of a cell membrane with a test agent also can be detected by detecting a change in RT activity in a relevant compartment, which can be in intracellular compartment or other compartment delimited by the cell membrane. RT activity can be measured using a polynucleotide template, which can be a DNA or an RNA template, or both. The RT being detected can be an RT that is present in a cell due, for example, to infection of the cell by a retrotransposable element that expresses the RT, or to expression in a cell of an exogenously added nucleic acid molecule encoding the RT, or can be that of an isolated RT polypeptide.

A method of the invention provides a means to examine test agents to identify those agents that can to modulate RT activity and/or alter divalent cation transporter activity. The term "test agent" is used herein to mean any compound that it to be examined for an ability to modulate RT activity and/or alter divalent cation (particularly manganese ion) transporter activity using a screening assay of the invention. A test agent can be a compound that is known to have such an ability, wherein the screening assay is used to confirm the activity, for example, with respect to a different transporter protein than one it is known to be able to alter; or to determine an amount of the agent that can be useful for modulating RT activity in a desired manner, for example, to reduce or inhibit the RT activity; or for standardizing the activity of the agent. A test agent also can be compound that is not known to have such activity and is being tested for such activity, thus providing a means to identify new agents potentially useful as drugs for modulating RT activity or for treating a disorder associated with undesirable divalent cation transporter activity. Such test agents can be agents that are based on an agent known to have an ability to modulate RT activity and/or alter divalent cation (particularly manganese ion) transporter activity, but that are modified, derivatized, or the like.

The term "agent" is used herein to refer to a test that is identified by the screening assay as having such an ability to modulate RT activity and/or alter divalent cation transporter activity. Such an agent, which can modulate RT activity, can be one that alters the transport of all cations that are transported by a particular divalent cation transporting protein, or, in particular, an agent that only alters manganese ion transport, but not any other divalent cations (if any) that can be transported by the divalent cation transporting protein. Further, the method can be used to identify an agent that reduces or inhibits manganese ion transport out of a cell, or that increases manganese transport into a cell, thus providing an agent that can increase an intracellular manganese ion concentration in a cell above a level normally found in the cell; or the method can be used to identify an agent that reduces or inhibits manganese ion transport into a cell, or that increase manganese ion transport out of a cell, thus providing an agent that can decrease an intracellular manganese ion concentration in a cell below a level normally found in the cell.

A test agent can be any type of molecule, for example, a polynucleotide, a peptide a peptidomimetic, peptoids such as vinylogous peptoids, a small organic molecule, or the like Polynucleotides, for example, are known to specifically interact with proteins and, therefore, can be useful as test agents to be screened for the ability to alter the activity of a divalent cation transporter. The term "polynucleotide" is used broadly herein to mean a sequence of two or more deoxyribonucleotides or ribonucleotides that are linked together by a phosphodiester bond. As such, the term "polynucleotide" includes RNA and DNA, which can be a synthetic RNA or DNA sequence, and can be single stranded or double stranded, as well as a DNA/RNA hybrid. Furthermore, the term "polynucleotide" as used herein includes naturally occurring nucleic acid molecules, which can be isolated from a cell, as well as synthetic molecules, which can be prepared, for example, by methods of chemical synthesis or by enzymatic methods such as by the polymerase chain reaction (PCR). In various embodiments, a polynucleotide useful as a test agent can contain nucleoside or nucleotide analogs, or a backbone bond other than a phosphodiester bond (see above).

In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucl. Acids Res.* 22: 5220-5234, 1994; Jellinek et al., *Biochemistry* 34: 11363-11372, 1995; Pagratis et al., *Nature Biotechnol.* 15: 68-73, 1997, each of which is incorporated herein by reference).

The covalent bond linking the nucleotides of a polynucleotide generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., *Nucl. Acids Res.* 22: 977-986, 1994; Ecker and Crooke, *BioTechnology* 13: 351360, 1995, each of which is incorporated herein by reference). The incorporation of non-naturally occurring nucleotide analogs or bonds linking the nucleotides or analogs can be particularly useful where the polynucleotide is to be exposed to an environment that can contain a nucleolytic activity, including, for example, a tissue culture medium or upon administration to a living subject, since the modified polynucleotides can be less susceptible to degradation.

A polynucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template (Jellinek et al., supra, 1995).

A peptide also can be useful as an agent that alters divalent cation transporter activity. The term "peptide" is used broadly herein to mean two or more amino acids linked by a peptide bond. Generally, a peptide useful in a method of the invention contains at least about two, three, four, five, or six amino acids, and can contain about ten, fifteen, twenty or more amino acids. As such, it should be recognized that the term "peptide" is not used herein to suggest a particular size or number of amino acids comprising the molecule, and that a peptide of the invention can contain up to several amino acid residues or more. Generally, however, smaller peptides are preferred where an identified agent is to be further examined, for example, for use as a drug for treating a subject. A peptide test agent can be prepared, for example, by a method of chemical synthesis, or can be expressed from a polynucleotide using recombinant DNA methodology. Where chemically synthesized, peptides containing one or more D-amino acids, or one or more amino acid analogs, for example, an amino acid that has been derivatized or otherwise modified at its reactive side chain, or in which one or more bonds linking the amino acids or amino acid analogs is modified, can be prepared. In addition, a reactive group at the amino terminus or the carboxy terminus or both can be modified. Such peptides can be modified, for example, to have improved stability to a protease, an oxidizing agent or other reactive material the peptide may encounter in a biological environment, and, therefore, can be particularly useful in performing a method of the invention. Of course, the peptides can be modified to have decreased stability in a biological environment such that the period of time the peptide is active in the environment is reduced.

As disclosed herein, the screening methods of the invention provide the advantage that they can be adapted to high throughput analysis and, therefore, can be used to screen combinatorial libraries of test agents in order to identify those agents that can alter divalent cation transporting protein activity. Methods for preparing a combinatorial library of molecules that can be tested for a desired activity are well known in the art and include, for example, methods of making a phage display library of peptides, which can be constrained peptides (see, for example, U.S. Pat. Nos. 5,622,699; 5,206, 347; Scott and Smith, *Science* 249: 386-390, 1992; Markland et al., *Gene* 109: 13-19, 1991; each of which is incorporated herein by reference); a peptide library (U.S. Pat. No. 5,264, 563, which is incorporated herein by reference); a peptidomimetic library (Blondelle et al., *Trends Anal. Chem.* 14: 83-92, 1995; a nucleic acid library (O'Connell et al., *Proc. Natl. Acad. Sci., USA* 93: 5883-5887, 1996; Tuerk and Gold, *Science* 249: 505-510, 1990; Gold et al., *Ann. Rev. Biochem.* 64: 763-797, 1995; each of which is incorporated herein by reference); an oligosaccharide library (York et al., *Carb. Res.,* 285: 99-128, 1996; Liang et al., *Science,* 274: 1520-1522, 1996; Ding et al., *Adv. Expt. Med. Biol.* 376: 261-269, 1995; each of which is incorporated herein by reference); a lipoprotein library (de Kruif et al., *FEBS Lett.* 399: 232-236, 1996, which is incorporated herein by reference); a glycoprotein or glycolipid library (Karaoglu et al., *J. Cell Biol.* 130: 567-577, 1995, which is incorporated herein by reference); or a chemical library containing, for example, drugs or other pharmaceutical agents (Gordon et al., J. Med. Chem. 37: 1385-1401, 1994; Ecker and Crooke, *BioTechnology* 13: 351-360, 1995; each of which is incorporated herein by reference). Polynucleotides can be particularly useful as agents that can modulate a specific interaction of myostatin and its receptor because nucleic acid molecules having binding specificity for cellular targets, including cellular polypeptides, exist naturally, and because synthetic molecules having such specificity can be readily prepared and identified (see, for example, U.S. Pat. No. 5,750,342, which is incorporated herein by reference).

In performing a screening assay of the invention in a high throughput format, isolated cell membranes or intact cells can be used. An advantage of using intact cells is that the method can be used, for example, to identify an agent useful for modulating RT activity in particular cells or cell types by altering manganese ion transport. For example, a plurality of human T lymphocytes isolated from a subject infected with HIV can be arranged in an array, which can be an addressable array, on a solid support such as a microchip, on a glass slide, on a bead, or in a well, and the cells can be contacted with different test agents to identify one or more agents having desirable characteristics, including, for example, in addition to the ability to alter manganese ion transport, minimal or no toxicity to the cell, desirable solubility characteristics, and the like. An additional advantage of arranging the samples in an array, particularly an addressable array, is that an automated system can be used for adding or removing reagents from one or more of the samples at various times, or for adding different reagents to particular samples. In addition to the convenience of examining multiple samples at the same time, such high throughput assays provide a means for examining duplicate, triplicate, or more aliquots of a single sample, thus increasing the validity of the results obtained, and for examining control samples under the same conditions as the test samples, thus providing an internal standard for comparing results from different assays.

Accordingly, the present invention also provides methods of modulating RT activity in a cell. Such a method can be performed, for example, by contacting the cell with an agent that alters manganese ion transport across a cell membrane of the cell, thereby modulating RT activity in the cell. The agent can be one that reduces or inhibits manganese ion transport out of the cell, particularly an agent that reduces or inhibits manganese ion transport across a cell membrane of the cell, but does not alter the transport of other divalent cations across the cell membrane. In addition, the invention provides methods of modulating RT activity by contacting the RT, under conditions suitable for reverse transcriptase activity, with a predetermined concentration of manganese ions. The conditions can be any conditions suitable for RT activity, including, for example, an in vitro reaction mixture containing a buffer, deoxyribonucleotide triphosphates, and/or a primer, and/or can include an extract of a cell, for example, an extract of a cell infected with a retrovirus. In one aspect, the method further includes contacting the RT with a predetermined concentration of magnesium ions, wherein the relative activity of a RT with respect to an RNA template as compared to a DNA template can be manipulated. Such a method can be useful, for example, for preferentially generating one strand of double stranded DNA corresponding to a retrovirus genome (i.e., the minus strand, in which case the RT is modulated such that it preferentially uses an RNA template, or the plus strand, in which case the RT is modulated such that it preferentially uses the minus strand as a template).

The present invention also relates to a method of ameliorating a retrovirus infection in a subject. Such a method can be performed, for example, by contacting cells of the subject with an agent that alters manganese ion transport in a retrovirus infected cell of the subject, thereby modulating (e.g., reducing or inhibiting) RT activity in the cells. The cells can be contacted with the agent in vivo, for example, by administering the agent systemically to the subject such that the agent circulates to the retrovirus infected cells, or by administering the agent at or near the site of the retrovirus infected cells in the subject. Alternatively, the cells can be contacted with the agent ex vivo, after which the cells can be expanded in culture without concern for replication of the retrovirus due to inhibition of the retrovirus reverse transcriptase, and uninfected cells of the expanded population can be selected and administered back into the subject. Preferably, the agent is one that reduces or inhibits a divalent cation transporting protein activity in the retrovirus infected cell, and more preferably, the agent does not alter transport of a divalent cation other than a manganese ion by the divalent cation transporting protein.

A subject to be treated according to a method of the invention can be any subject that is susceptible to infection with a retrovirus, and particularly a subject in the which the infection has a deleterious effect. In particular, the subject can be a human or other mammalian subject in which the retroviral infection, for example, adversely disrupts a gene in the genome of cells of the subject due to random integration into the genome, thus resulting in a loss of function of the gene; or integrates into a gene in the genome of cells and adversely increases the expression of the gene, thereby resulting in increased expression of all or a portion of the encoded gene product (e.g., an activated oncogene); or otherwise results in a pathologic condition, such as infection with HIV-1, which can cause AIDS. The subject to be treated according to a method of the invention also can be domesticated or farm animal, or the like, for example, poultry infected with avian myeloblastosis virus, or cats infected with feline leukemia virus.

For administration to a subject, an agent that modulates RT activity, particularly by altering manganese ion levels in cells infected with the retrovirus is administered by a route and under conditions that facilitate contact of the agent with the target cell and, if appropriate, entry into the cell. Thus, the agent can be administered to the site of the cells to be treated, or can be administered by any method that provides the target cells with the agent. Furthermore, the agent generally is formulated in a composition (e.g., a pharmaceutical composition) suitable for administration to the subject. As such, the invention provides pharmaceutical compositions containing an agent, which is useful for altering manganese transport in a cell, in a pharmaceutically acceptable carrier. As such, the agents are useful as medicaments for treating a subject suffering from a pathological condition as defined herein. Further, such a composition can include one or more other compounds that, alone or in combination with the agent that manganese transport, provides a therapeutic advantage to the subject, for example, an antibiotic if the subject is susceptible to a bacterial infection, one or more additional antiviral agents known to be useful for treating the retrovirus infecting the cells of the subject, a nutrient or vitamin or the like, a diagnostic reagent, toxin, a therapeutic agent such as a cancer chemotherapeutic agent, or any other compound as desired, provided the additional compound(s) does not adversely affect the activity of the agent that alters manganese transport or, if the compound does affect the activity of the agent, does so in a manner that is predictable and can be accounted for in formulating the agent that alters manganese transport.

A composition of the invention generally contains the agent formulated with one or more other pharmaceutically acceptable carriers, which are well known in the art and include, for example, aqueous solutions such as water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the physico-chemical characteristics of the agent that alters manganese transport and on the route of administration of the composition, which can be, for example, orally or parenterally such as intravenously, and by injection, intubation, or other such method known in the art.

The agent that modulates RT activity by altering manganese transport in cells infected with a retrovirus can be incorporated within an encapsulating material such as into an oil-in-water emulsion, a microemulsion, micelle, mixed micelle, liposome, microsphere or other polymer matrix (see, for example, Gregoriadis, *Liposome Technology*, Vol. 1 (CRC Press, Boca Raton, Fla. 1984); Fraley et al., *Trends Biochem. Sci.* 6: 77, 1981, each of which is incorporated herein by reference). Liposomes, for example, which consist of phospholipids or other lipids, are nontoxic, physiologically acceptable and metabolizable carriers that are relatively simple to make and administer. "Stealth" liposomes (see, for example, U.S. Pat. Nos. 5,882,679; 5,395,619; and 5,225,212, each of which is incorporated herein by reference) are an example of such encapsulating materials particularly useful for preparing a composition useful for practicing a method of the invention, and other "masked" liposomes similarly can be used, such liposomes extending the time that the therapeutic agent remain in the circulation. Cationic liposomes, for example, also can be modified with specific receptors or ligands (Morishita et al., *J. Clin. Invest.* 91: 2580-2585, 1993, which is incorporated herein by reference). In addition, a polynucleotide agent can be introduced into a cell using, for example, adenovirus-polylysine DNA complexes (see, for example, Michael et al., *J. Biol. Chem.* 268: 6866-6869, 1993, which is incorporated herein by reference).

The route of administration of a pharmaceutical composition containing an agent that modulates RT activity will depend, in part, on the chemical structure of the molecule. Polypeptides and polynucleotides, for example, are not particularly useful when administered orally because they can be degraded in the digestive tract. However, methods for chemically modifying polypeptides, for example, to render them less susceptible to degradation by endogenous proteases or more absorbable through the alimentary tract are well known (see, for example, Blondelle et al., supra, 1995; Ecker and Crook, supra, 1995). In addition, a peptide agent can be prepared using D-amino acids, or can contain one or more domains based on peptidomimetics, which are organic molecules that mimic the structure of peptide domain; or based on a peptoid such as a vinylogous peptoid.

A pharmaceutical composition as disclosed herein can be administered to an individual by various routes including, for example, orally or parenterally, such as intravenously, intramuscularly, subcutaneously, intraorbitally, intracapsularly, intraperitoneally, intrarectally, intracisternally or by passive or facilitated absorption through the skin using, for example, a skin patch or transdermal iontophoresis, respectively. Furthermore, the pharmaceutical composition can be administered by injection, intubation, orally or topically, the latter of which can be passive, for example, by direct application of an ointment, or active, for example, using a nasal spray or inhalant, in which case one component of the composition is an appropriate propellant. A pharmaceutical composition also can be administered to the site of a pathologic condition, for example, intravenously or intra-arterially into a blood vessel supplying a tissue or organ comprising retrovirus infected cells.

The pharmaceutical composition also can be formulated for oral formulation, such as a tablet, or a solution or suspension form; or can comprise an admixture with an organic or inorganic carrier or excipient suitable for enteral or parenteral applications, and can be compounded, for example, with the usual non-toxic, pharmaceutically acceptable carriers for tablets, pellets, capsules, suppositories, solutions, emulsions, suspensions, or other form suitable for use. The carriers, in addition to those disclosed above, can include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening or coloring agents and perfumes can be used, for example a stabilizing dry agent such as triulose (see, for example, U.S. Pat. No. 5,314,695).

The total amount of an agent to be administered in practicing a method of the invention can be administered to a subject as a single dose, either as a bolus or by infusion over a relatively short period of time, or can be administered using a fractionated treatment protocol, in which multiple doses are administered over a prolonged period of time. An advantage of using a fractionated method is that, upon normal division of a retrovirus infected cell, replication of the retrovirus can be reduced or inhibited due to the presence of the agent. One skilled in the art would know that the amount of the composition to treat a retrovirus infection in a subject depends on many factors including the age and general health of the subject as well as the route of administration and the number of treatments to be administered. In view of these factors, the skilled artisan would adjust the particular dose as necessary. In general, the formulation of the pharmaceutical composition and the routes and frequency of administration for treatment of human subjects are determined, initially, using Phase I and Phase II clinical trials.

The following examples are intended to illustrate but not limit the invention.

EXAMPLE 1

Strains and media. The strains used in this study were JB740 (MATαhis3Δ200Δleu2 1 ura3-167), yEB104A (JB740 with pmr1Δ::hphMX4), YH8 (MATαhis3Δ200 leu2Δ1 trp1Δ1 ura3-167; Chapman and Boeke, *Cell* 65: 483492, 1991, which is incorporated herein by reference), which is incorporated herein by reference), YH23 (YH8 transformed with plasmid pX3) (Chapman and Boeke, supra, 1991), KM255 (transposition-deficient mutant of YH23). Media were prepared as described by Sherman et al. (*Methods in yeast genetics* (Cold Spring Harbor Laboratory Press, 1986), which is incorporated herein by reference. $Mn^{2+}$ hypersensitivity was tested by growth on plates containing synthetic complete (SC) medium supplemented with 3 mM $MnCl_2$ (Wei et al., *Biochemistry* 38: 14534-14541, 1999, which is incorporated herein by reference).

Plasmid constructions. Plasmid c24-2I was generated by ligating the Stu I -Avr II fragment (4.3 kb) of c24-2 with the Sma I—Xba I fragment (6.0 kb) of pRS415 (LEU2 CEN6; Sikorski and Hieter, *Genetics* 122: 19-27, 1989, which is incorporated herein by reference). To simplify the cloning of the single amino-acid-substitution mutations into the PMR1 gene, c24-2L was constructed by removing the Xho I—Nde I fragment (1.2 kb) from c24-2I, filling in the ends with Klenow (New England Biolabs; Beverly Mass.), and ligating the blunt ends to recircularize the plasmid. Alanine substitution mutations, D778A and Q783A, were generated in the native PMR1 gene by replacing the Pst I—Sal I fragment (1.1 kb) of c24-2L with the corresponding fragment harboring the respective Pmr1p substitution mutation in the YEpHR1 backbone (Wei et al., *J. Biol. Chem.* 275: 23927-23932, 2000, which is incorporated herein by reference). The D53A substitution mutation was introduced into c24-2L by swapping in the Xba I fragment (0.3 kb) containing the Pmr1p substitution mutation in the YEpHR1 backbone (Wei et al., supra, 1999). Recombinant Ty1 RT (Wilhelm et al., supra, 2000) was PCR amplified and subcloned into the BamH I and Xho I sites of pGEX-4T-3 (Amersham Pharmacia Biotech; Piscataway N.J.). The D211N substitution mutation was generated by replacing the Sph I-Hind III fragment (0.4 kb) of the wild-type Ty1 RT expression construct with that of pJEF724 DD-DN (Uzun and Gabriel, supra, 2001).

RNA isolation and blot analysis. Total RNA was isolated from 10 ml cultures of yeast grown in YNB supplemented with 1% casamino acids and 1% raffinose at 30° C. for about 6 hr. Glucose (represses) or galactose (induces pGal-Ty1 expression and transposition) was added to 2% and cultures were grown at 22° C. for 42 hr. Strains included YH8 transformed with pB656 (pGal vector lacking Ty1 sequence), YH23, KM255 and EBX10A-2B. Total RNA was extracted by hot acid phenyl (Collart and Oliviero, In *Current Protocols in Molecular Biology* (eds. Ausubel et al., John Wiley & Sons 1993), which is incorporated herein by reference) and fractionated by denaturing gel electrophoresis as described below.

For quantification of ACT1 and Ty1-TRP1 RNAs, 20 µg total RNA was heat denatured in sample buffer (55% deionized formamide, MOPS buffer, pH 7.0, 5% formaldehyde, 8 mM EDTA) and 0.1% bromophenyl blue) before electrophoresis on 1% agarose gels containing MOPS buffer, pH 7.0 (40 mM MOPS, 10 mM sodium acetate and 1 mM EDTA) and 2% formaldehyde. RNA was transferred by capillary action and fixed by UV crosslinking to Gene Screen Plus™ filters as described by the manufacturer (NEN Life Science Products, Inc.; Boston Mass.). Membrane-bound RNAs were hybridized to ACT1-specific (1.2 kb BamH I—Hind III fragment of pΔ10-AHX3) and TRP1-specific (1 kb BamH I fragment of pX8) DNA probes that were internally labeled and purified over G25 Sephadex spin columns. Filters were exposed to a Molecular Dynamics phosphoimager screen. Quantification of the relative steady-state transcripts (ratio of Ty1-TRP1/ACT1) was done using a STORM Imaging System with ImageQuant v1.11 (Molecular Dynamics) and Microsoft Excel software.

Transposition assay. Yeast transformants containing the URA3 Ty1-TRP1 donor plasmid, pX3 (pGal-Ty1 element marked with TRP1; Xu and Boeke., *Proc. Natl. Acad. Sci., USA* 84: 8553-8557, 1987, which is incorporated herein by reference), and any of the LEU2 CEN-based vectors were patched onto SC medium lacking leucine, tryptophan and uracil (SC-Leu-Trp-Ura) with 2% glucose. After 2-3 days at 30° C., yeast patches were replica plated to SC-Leu-Ura with 2% galactose and incubated at 22° C. for 3 days. The Ty1 donor plasmid was shuffled out by growth on SC-Leu with 2% glucose at 30° C. overnight followed by growth on SC-Leu-Trp containing 1 g/L of 5-fluoro-orotic acid (5-FOA) (Boeke et al., *Mol. Gen. Genet.* 197: 345-346, 1984) with 2% glucose at 30° C. for 2 days (selective growth for cells containing a transposed copy of Ty1-TRP1).

Transformants containing the URA3-marked Ty1 donor plasmid, pGTy1-H3-mhis3AI (Curcio and Garfinlcel, *Proc. Natl. Acad. Sci., USA* 88: 936-940, 1991, which is incorporated herein by reference), and any of the LEU2 CEN-based vectors were spotted onto SC-Leu-Ura with 2% glucose. After 2 days at 30° C., yeast spots were replica plated to similar medium with 2% galactose and incubated at 22° C. for 3 days. At this point Ty1 transposition was assayed by using either single-step (non-5-FOA) selection or 5-FOA selection. Yeast spots to be analyzed by single-step selection were resuspended in sterile water to an $OD_{600}=1.0$, and 5-fold serial dilutions were spotted onto SC-Leu-His (lacks histidine) with 2% glucose (selective growth for cells containing a transposed copy of the HIS3-marked Ty1 element). In yeast spots to be analyzed by 5-FOA selection, the Ty1 donor plasmid was shuffled out as discussed above, except 5-FOA-containing medium was SC-Leu-His.

cDNA analysis. Lawns of yeast cotransformed with pGTy1-H3-mhis3AI and various LEU2 CEN-based vectors were scraped from SC-Leu-Ura plates with 2% glucose and resuspended in 10 ml of YNB medium containing 1% casamino acids and 1% raffinose. Cells were grown at 30° C. for approximately 6 hr to exhaust remaining glucose. Galactose was then added to 2% and cultures were incubated at 22° C. for 24 hr. Cells were harvested as described (Lawler et al., *J. Virol.* 75: 6769-6775, 2001, which is incorporated herein by reference), genomic DNA was isolated (Boeke et al., *Cell* 40: 491-500, 1985, which is incorporated herein by reference) from 11 ml cultures, then digested with Afl II. DNA fragments were fractionated by agarose gel electrophoresis and transferred to Gene Screen Plus™ filters. Hybridization was measured using a Molecular Dynamics phosphoimager. The ratio of HIS3-specific hybridization for the Ty1 cDNA fragment (2.2 kb) relative to that of the pGTy1-H3-mhis3AI fragment (14.3 kb) provided a measure of the amount of Ty1 cDNA.

VLP isolation and analysis. Yeast cells harboring pGTy1-H3-mhis3AI were grown in 2% galactose at 22° C. for approximately 24 hr. Cell pellets from these 0.5 L cultures were resuspended in 5 ml buffer B (Eichinger and Boeke, *Cell* 54: 955-966, 1988, which is incorporated herein by reference) and VLPs were isolated. VLP-associated RT activity was measured for sucrose gradient fractions 21-28 as described (Eichinger and Boeke, supra, 1988), except that 3 µl of VLPs in buffer B (no EDTA) were used in 30 µl reactions (50 mM HEPES-KOH, pH 7.8, 3 mM DTT, 0.2 µM dGTP, 0.5 µCi of $\{\alpha^{32}P\}$-dGTP, 1 µg/ml oligo(dG)$_{12-18}$, 10 µg/ml poly (rC)$_n$ and the indicated concentrations of $MgCl_2$ and/or $MnCl_2$). Reactions were set up on ice, carried out for 1 hr at 22° C. and kept on ice while being spotted onto DE81 anion-exchange paper (Whatman International Ltd.; Maidstone, England).

Immunoblot analysis was performed on gradient fractions to normalize the RT activity of each fraction by the amount of Ty1 RT in the fraction. For detection of IN (integrase), RT and Gag, 2 µl, 2 µl and 0.1 µl, respectively, of each gradient fraction were boiled in SDS-PAGE sample buffer and run onto 5% stacking/10% separating SDS polyacrylamide gels. Proteins were transferred onto 0.45 µm PVDF membranes (IMMOBILON-P; Millipore Corp.; Bedford Mass.) in transfer buffer (25 mM Tris base, 192 mM glycine, and 20% methanol) at 25 V for 12-16 hr. Filters were washed 4 times (10 min each) with 10 ml blocking buffer (Tris-buffered saline containing 1% non-fat milk and 0.1% TWEEN 20 detergent) and incubated for 1 hr with the indicated antibodies (1/1,000 dilution of 8B11 to detect IN, 1/1,000 dilution of JB3904-N to detect RT, and 1/20,000 dilution of R2-F to detect Gag) in 10 ml blocking buffer. Membranes were washed as indicated above and incubated for 1 hr with 1/10,000 dilutions of alkaline phosphatase-conjugated donkey anti-rabbit (detection of RT and Gag) or anti-mouse (detection of 1N) 1 gG (Pierce; Rockford Ill.) in 10 ml blocking buffer. Immunoblots were washed again as indicated, visualized by enhanced chemifluorescence (ECF reagent) development (Amersham) and quantified on a STORM Imaging System with ImageQuant v1.11 (Molecular Dynamics) and Microsoft Excel™ software.

Protein purification and analysis. Recombinant Ty1 RT (Wilhelm et al., supra, 2000) containing a cleavable N-terminal GST-tag was expressed in *E. coli* and purified first by affinity chromatography and then by ion exchange chromatography, as described for HIV-1 RT (Le Grice et al., *Meth. Enzymol.* 262: 130-44, 1995, which is incorporated herein by reference). The GST-tagged protein was eluted from a Glutathione Sepharose 4B™ gel (Amersham) gravity column with buffer (50 mM HEPES-KOH, pH 7.8, 200 mM KCl, 10% glycerol and 2 mM DTT) containing 30 mM reduced glutathione. 50 mM HEPES-KOH, pH 7.0 with 10% glycerol was added to the protein solution to lower the pH to 7.1 and the KCl concentration to 25 mM. The recombinant Ty1 RT was further purified over a Resource S™ (Amersham) cation-exchange column using a linear KCl gradient (25-500 mM). Recombinant Ty1 RT eluted from the Resource S™ column in approximately 250 mM KCl. Purified hetero-dimeric HIV-1 RT (Le Grice et al., supra, 1995) was acquired through the AIDS Research and Reference Reagent Program, Division of AIDS, NIAID, NIH. Purified AMV RT was purchased from Roche Molecular Biochemicals (Mannheim, Germany). The RT assays performed on the purified RTs were carried out as described above, except in the presence of 20 mM KCl, and HIV-1 RT assays were incubated at 37° C. Each reaction contained 45 ng of purified recombinant Ty1 RT or 30 ng of heterodimeric HIV-1 RT. Under these conditions, the velocity of the reaction was linear with time and enzyme concentration.

Results

Isolation and identification of the PMR1 gene. A genetic screen was previously developed (Xu and Boeke., supra, 1990) to identify cellular components involved in Ty1 transposition. In one application of this screen (Chapman, In *Molecular Biology and Genetics* (The Johns Hopkins University School of Medicine Press 1991), pages 85 et seq., 1991, which is incorporated herein by reference; Chapman and Boeke, supra, 1991), yeast strain YH23 (Chapman and Boeke, supra, 1991) containing the URA3 Ty1-TRP1 donor plasmid, pX3 (pGal-Ty1 element marked with TRP1; Xu and Boeke, supra, 1987), was mutagenized with ethyl methanesulfate (EMS) and screened for transposition defects. The transposition assay consists of a series of replica-plating steps, in which pGal-Ty1 expression and transposition is induced on galactose containing media, and then scored by quantifying the number of Trp$^+$ plasmid-free colonies. One of the most severe and stable transposition-deficient mutants, KM255 (derived by EMS mutagenesis of strain YH23; Chapman, supra, 1991), was characterized.

Figure 2:
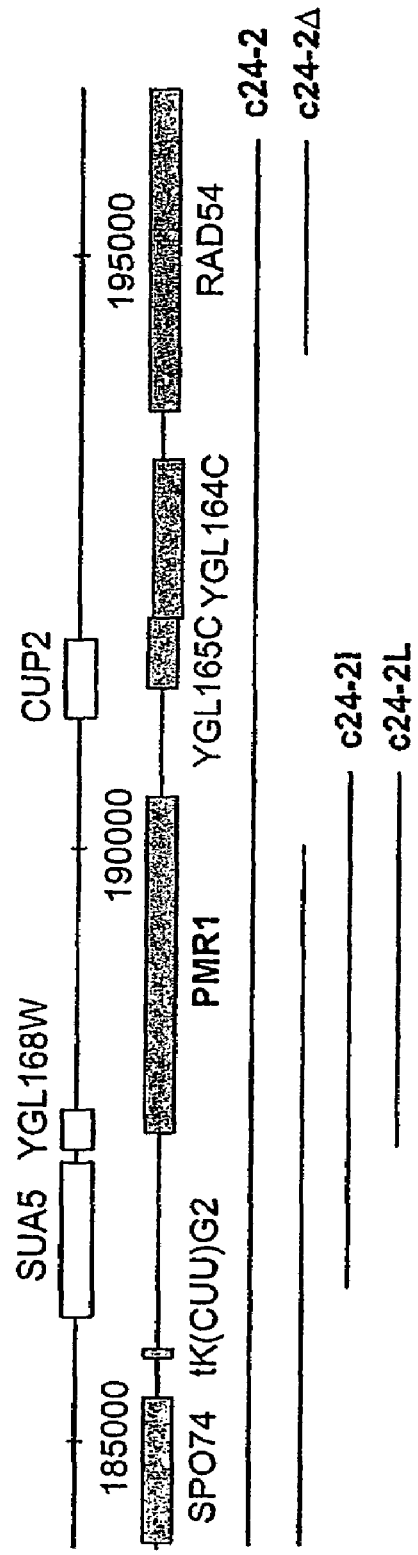
FIG. 2 illustrates the PMR1 locus, the insert contained within c24-2 and subsequent subclones (see Example 1). Open boxes represent genes transcribed from left to right, and gray boxes represent genes transcribed from right to left. Coordinates (base pairs; bp) are those assigned by SGD (see world wide web, hypertext transport protocol "genome-www.stanford.edu/*Saccharomyces*/") for chromosome seven.

The KM255 mutation was recessive and was backcrossed, generating spore clone EBX10A-2B, which was used to isolate the relevant gene by complementation cloning. EBX10A-2B, harboring a galactose inducible TRP1-marked Ty1 element, pX3 was transformed with a LEU2-CEN4-based genomic library. Approximately 5,900 of the resulting transformants were assayed for their transposition phenotype. A single genomic clone, c24-2 (FIG. 2), complemented the aberrant transposition phenotype of EBX10A-2B. Sequence analysis of the clone identified the insert as an 11.8 kb fragment of chromosome VII encoding eight predicted open reading frames (ORFs). Subsequent subdivision 8 of the 11.8 kb insert identified a 4.3 kb fragment, c24-2I, and a smaller 3.1 kb subfragment containing only the full-length PMR1 gene, c24-2L (see FIG. 2), that fully complemented the transposition phenotype. The mutant transposition phenotype was recapitulated in a strain in which the endogenous PMR1 ORF was completely replaced by the hygromycin B resistance cassette, hphMX4 (Goldstein and McCusker, *Yeast* 15: 1541-1553, 1999, which is incorporated herein by reference). Supplying PMR1 episomally in clones c24-2 and c24-2I completely complemented the transposition defect of the pmr1Δ::hphMX4 (pmr1Δ) strain. Furthermore, both haploid parents and all tested diploids that resulted from crossing EBX10A-2B with the pmr1Δ strain were hypersensitive to $Mn^{2+}$, whereas diploids produced by crossing EBX10A-2B with JB740 (PMR1) were not hypersensitive to $Mn^{2+}$. This result indicates that the original mutation present in EBX10A-2B resides within PMR1.

Disrupting $Mn^{2+}$ transport of Pmr1p decreases Ty1 transposition. Since cells lacking PMR1 were found to specifically accumulate $Mn^{2+}$ and $Ca^{2+}$ (Lapinskas et al., *Mol. Cell. Biol.* 15: 1382-1388, 1995, which is incorporated herein by reference), an examination was made as to whether the accumulation of either $Mn^{2+}$ or $Ca^{2+}$ was responsible for the transposition defect. To do this, three Pmr1p single-amino-acid-substitution mutations were assayed for their ability to complement the transposition phenotype of the pmr1Δ strain. The Q783A mutation in Pmr1p specifically abolishes $Mn^{2+}$ transport, whereas the D53A mutation prevents $Ca^{2+}$ transport. The D778A mutation abrogates both transport activities (Wei et al., *J. Biol. Chem.* 275: 23927-23932, 2000; Wei et al., *Biochemistry* 38: 14534-14541, 1999, each of which is incorporated herein by reference). Yeast expressing Pmr1p with either the Q783A or the D778A mutation (both of which abolish $Mn^{2+}$ transport) displayed the mutant transposition phenotype, whereas cells producing Pmr1p with the D53A mutation (normal $Mn^{2+}$ transport) showed a wild-type transposition phenotype. Ty1 transposition was only deficient in those mutants unable to transport $Mn^{2+}$ into the secretory pathway, indicating that the aberrant transposition phenotype is due to cytosolic accumulation of $Mn^{2+}$.

Synthesis of Ty1 cDNA is decreased in cells lacking PMR1. In order to identify the point in the Ty1 lifecycle (expression and VLP assembly, reverse transcription, or integration) at which the transposition block occurred, the relative steady-state levels of marked-Ty1 RNA in the wild-type and pmr1Δ mutant cells were verified to be equivalent. To assess whether cDNA was being synthesized in pmr1Δ cells, genomic DNA was isolated from isogenic strains grown under pGal-Ty1-inducing conditions and relative steady-state levels of Ty1 cDNA were measured. PMR1 cells produced at least 50-fold more Ty1 cDNA than pmr1Δ cells. Moreover, cells expressing mutant forms of Pmr1p unable to transport $Mn^{2+}$, D778A and Q783A, produced nearly 20-fold less Ty1 cDNA than cells able to transport $Mn^{2+}$, wild-type Pmr1p and the D53A mutant. These results indicate that transposition in pmr1Δ mutants is hindered at a point between translation of the Ty1 proteins and the end of cDNA synthesis.

VLPs are made in cells lacking PMR1. In order to discern whether the transposition defect in pmr1Δ cells resulted from altered protein components and/or VLP assembly, VLPs were isolated from PMR1 and pmr1Δ cells. Immunoblot analyses and RT assays were performed on fractions from the density gradients on which the VLPs were purified. The amounts of Ty1 RT and Gag present in both sets of VLPs were nearly identical for both sets of VLPs (see FIG. 3A). While the amounts of integrase in fractions 21-22 and 27-28 were slightly less for the VLPs isolated from pmr1Δ cells, the amounts present in the peak fractions for RT activity were nearly identical to those of the VLPs isolated from the PMR1 cells (FIG. 3A); the small variations observed are typical experimental variations seen with this technique. Thus, similar amounts of normally assembled VLPs are made in PMR1 and pmr1Δ cells. Moreover, the absence of any high molecular weight species on the immunoblots, together with the normal ratio of precursor (p49) to processed (p45) Gag, suggested that the VLP-associated Ty1 proteins isolated from pmr1Δ cells were processed by the Ty1 protease similarly to those found in VLPs isolated from PMR1 cells.

Figure 3:
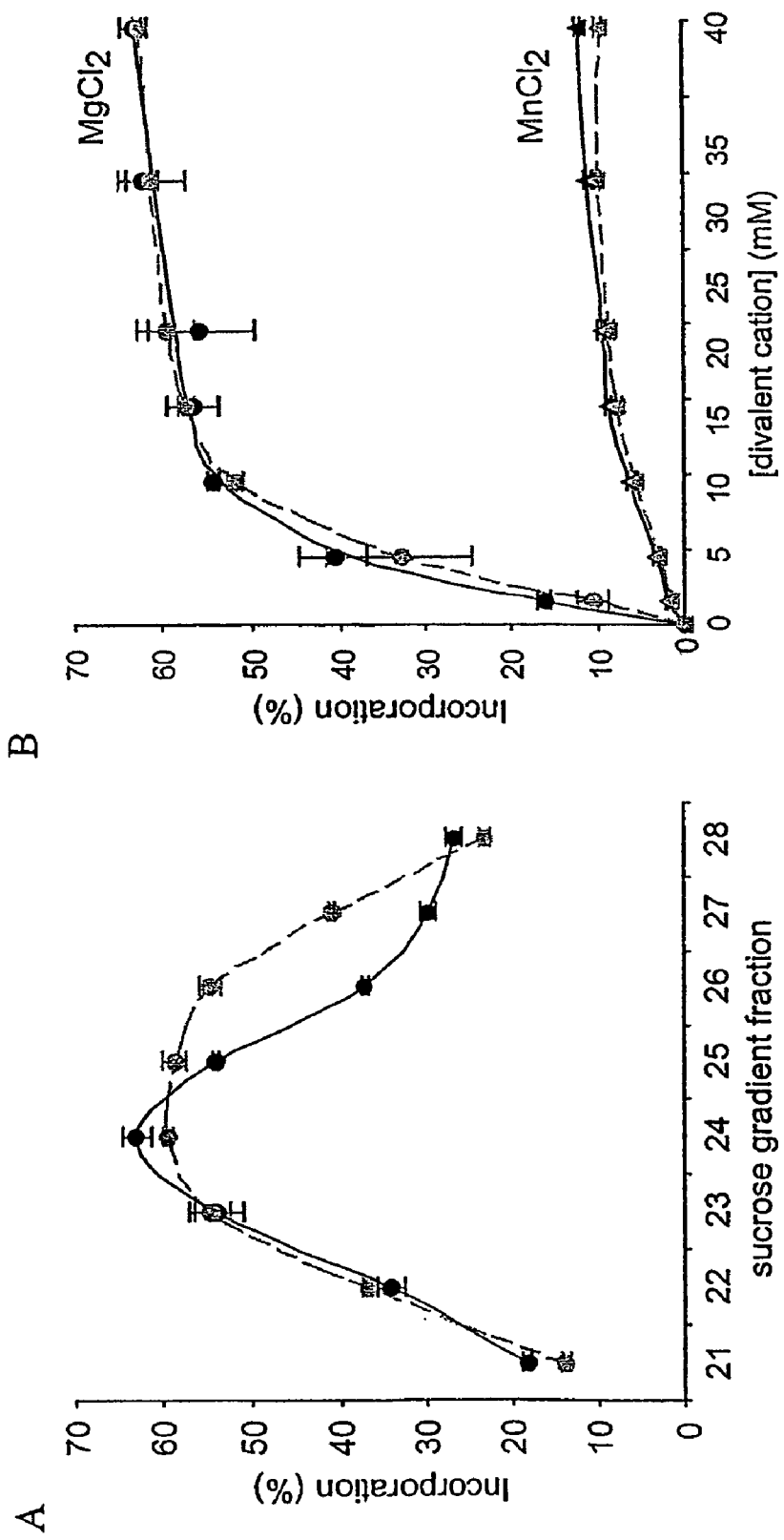
FIGS. 3A and 3B show a characterization of VLPs isolated from wild-type (PMR1) and pmr1Δ cells. Quantitative immunoblotting of sucrose gradient fractions was performed using anti-integrase, anti-reverse transcriptase, and anti-Gag antibodies.

$Mn^{2+}$ inhibits in vitro RT activity even in excess $Mg^{2+}$. To determine whether $Mn^{2+}$ could directly alter the activity of Ty1 RT, in vitro reverse transcription assays were performed using VLPs isolated from PMR1 and pmr1Δ cells. VLPs isolated from pmr1Δ cells incorporated radiolabeled dGTP into the primer-template $(dG)^{12-18}$-poly(rC) at a rate similar to VLPs isolated from wild-type (PMR1) cells (FIG. 3B). Moreover, the RT activity associated with both sets of VLPs was decreased to similar extents when $Mn^{2+}$ was substituted for $Mg^{2+}$ as the divalent cation. Therefore, Ty1 RT produced in pmr1Δ mutant cells was indistinguishable from RT present in wild-type cells. These results indicate that $Mn^{2+}$ directly affects the process of reverse transcription, and possibly the RT itself, since RT is a metal-dependent polymerase.

Figure 4:
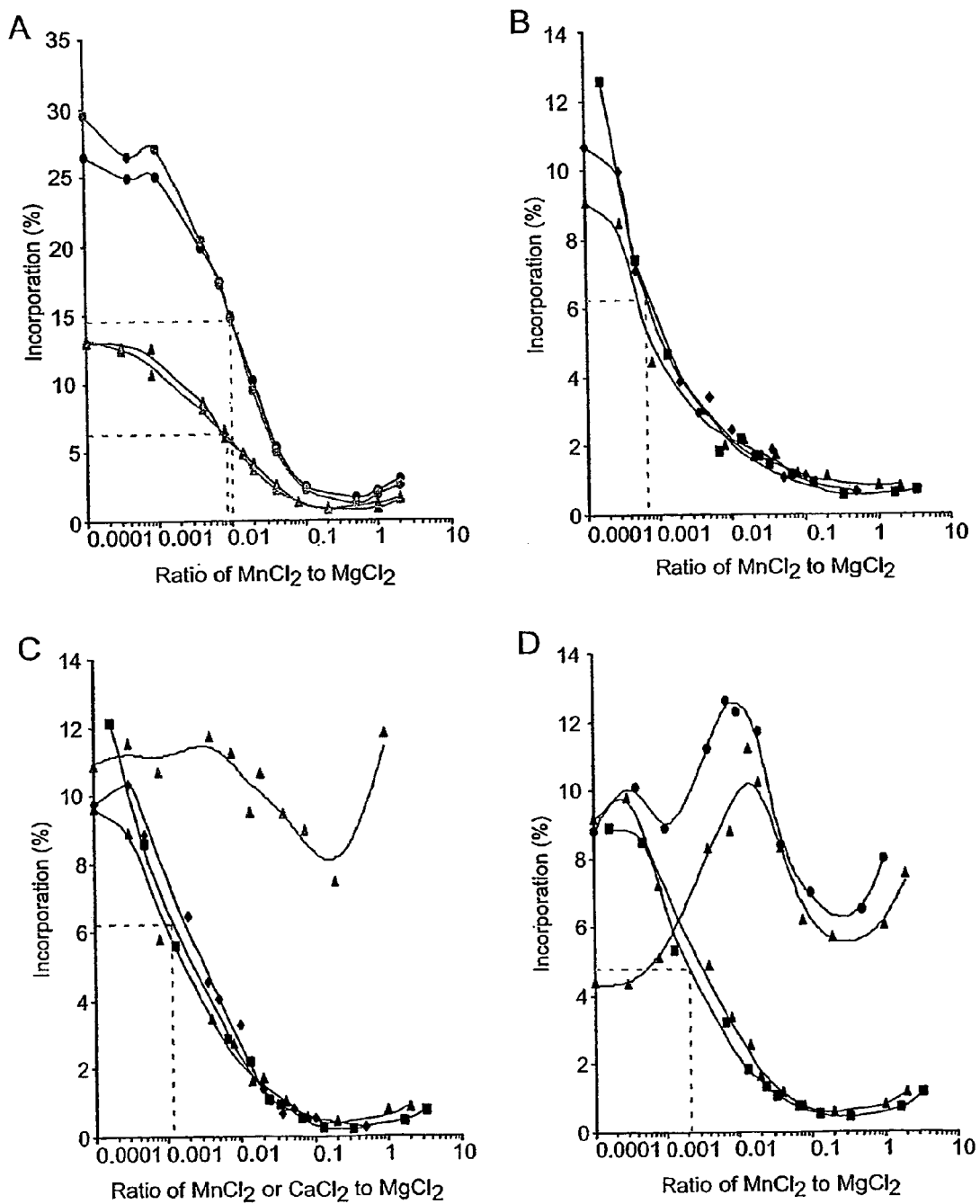
FIG. 4 illustrates $Mn^{2+}$-dependent inhibition of RNA-directed DNA polymerization. Reactions were performed with 10 mM (circles), 5 mM (triangles), 3 mM (squares), or 2 mM (diamonds) $MgCl_2$ and varying concentrations (0.2 μM-20 mM) of $MnCl_2$ (black and red lines) or $CaCl_2$ (green line). VLPs were isolated from wild-type cells (black lines) and pmr1Δ cells (gray lines). 100% incorporation corresponds to 5 pmol dGTP incorporated/μl of VLPs, 137 pmol dGTP incorporated/μg Ty1 RT, and 205 pmol dGTP incorporated/μg HIV-1 RT during the 60 min RT assays. Straight dashed gray lines indicate half-maximal incorporation conditions.

Competition experiments between $Mn^{2+}$ and $Mg^{2+}$ (FIG. 4) showed that exceedingly low levels of $Mn^{2+}$ inhibited the RNA-directed DNA polymerase activity of VLPs in the presence of excess $Mg^{2+}$ regardless of whether the VLPs were obtained from wild-type or pmr1Δ cells (FIG. 4A). Even more dramatic $Mn^{2+}$-dependent inhibition was observed for purified hetero-dimeric HUV-1 RT (FIG. 4B), purified AMV RT and purified recombinant Ty1 RT (FIG. 4C). An earlier study hinted that the RT in HIV-1 virions, but not homodimeric HIV-1 RT, was sensitive to $Mn^{2+}$ in vitro (Filler and Lever, *AIDS Res. Hum. Retroviruses* 13: 291-299, 1997, which is incorporated herein by reference). Since RTs are active on both RNA and DNA templates, and both activities are required for replication, it was important to determine the effect of $Mn^{2+}$ on both templates. $Mn^{2+}$-dependent inhibition was also observed when a DNA template (poly(dC)) was substituted for poly(rC), for both Ty1 VLPs and purified recombinant Ty1 RT, although the extent of inhibition was slightly less dramatic with the DNA template. Inhibition of Ty1 RT was $Mn^{2+}$-specific; when a control competition experiment was conducted, in which $Ca^{2+}$ was substituted for $Mn^{2+}$, no significant inhibition was observed (FIG. 4C). Ratios of $Mn^{2+}$ to $Mg^{2+}$ that reduced RT activity by 50% were calculated and ranged from as low as $7\times10^{-4}$ for HIV-1 RT to $1\times10^{-3}$ for Ty1 RT and to $8\times10^{-3}$ for Ty1 VLPs. Thus, very small quantities of $Mn^{2+}$ had a profound impact on RT activity in vitro.

An RT mutant insensitive to $Mn^{2+}$-dependent inhibition in vitro. While structural studies led to the proposed two metal model for DNA polymerization, they are speculative and offer little information about the kinetic properties at the two metal-binding sites (sites A and B; see FIG. 1). To discern which of the metal-binding sites contribute most to the catalytic activity of RT and which site is responsible for the $Mn^{2+}$-dependent inhibition, the A site was specifically perturbed. A previous study found that Ty1 VLPs containing a mutant form of the RT with an asparagine replacing an invariant aspartate at position 211 (D211N) could carry out reverse transcription in vitro (Uzun and Gabriel, supra, 2001). Based on the fact that the mutant residue is coordinated to metal A, the effect of the D211N mutation is mostly if not entirely on the divalent cation at the A site (FIG. 1). Compared to wild-type (Wt) Ty1 RT, the D211N Ty1 RT was not inhibited by increasing concentrations of $Mn_{2+}$ in the presence of excess $Mn^{2+}$ (FIG. 4D). In fact, the modest increase in activity seen when $Mn^{2+}$ is added to D211N RT, which peaks at a ratio of 0.02 ($Mn^{2+}$ concentration to $Mg^{2+}$ concentration), likely resulted from saturating the partially occupied A site (see below). Increased activity at low $Mn^{2+}$ concentrations was also observed for purified M-MuLV RT, with or without its associated RNase H, which incorporated slightly more radio-labeled dGTP into the primer-template as $Mn^{2+}$ concentrations increased. These results indicate that $Mn^{2+}$ affected the RT enzyme and not the primer-template or dNTP substrates, and further indicate that the B site divalent cation is a major determinant of RT catalytic activity.

The D211N mutation in Ty1 RT was shown to abolish transposition in vivo (Uzun and Gabriel, supra, 2001). Because the D211N mutant RT was insensitive to increasing concentrations of $Mn^{2+}$ in the presence of excess $Mg^{2+}$, the transposition of a Ty1 element containing D211N RT was examined in pmr1Δ cells. Wild-type and D211N RT Ty1 elements transposed equally poorly in pmr1Δ cells. This was not unexpected because the D211N RT previously was reported to prevent the completion of cDNA synthesis and not the initiation of minus strand strong stop synthesis (Uzun and Gabriel, supra, 2001).

Cooperativity of divalent metal ion binding for RTs. To further investigate the metal-dependent activity of purified recombinant Ty1 RT, kinetic analyses was performed on the wild-type and D211N RTs. At fixed substrate concentrations, $Mg^{2+}$ activated the wild-type (FIG. 5A) and the D211N (FIG. 5B) RTs, and for both enzymes the $Mg^{2+}$-dependent activation curves were sigmoidal. A similar sigmoidal activation curve was observed for purified hetero-dimeric HUV-1 RT. Moreover, $Mn^{2+}$ activated the wild-type (FIG. 5C) and D211N (FIG. 5D) Ty1 RTs. For both enzymes, the $Mn^{2+}$-dependent activation curves were also sigmoidal. From inspection of the four activation curves, it was evident that much more $Mg^{2+}$ was needed to achieve half maximal activity for the D211N RT compared to the wild-type RT. Conversely, much less $Mn^{2+}$ is required to reach peak activity for the D211N RT relative to the wild-type RT. The sigmoidal activation curves precluded direct determination of Michaelis constants for $Mg^{2+}$ and $Mn^{2+}$.

However, a fit of the data to the Hill equation yielded the average Hill coefficient (n), the macroscopic dissociation constants ($K_{0.5}$) and the maximum velocity or catalytic turnover ($k_{cat}$) for each divalent cation with each RT (summarized in Table 1). While the wild-type and D211N Ty1 RTs support similar maximal velocities for their preferred metal ion, they have very different affinities for that same metal ion. The wild-type RT has 50-fold higher affinity for $Mg^{2+}$ than does D211N RT. In contrast, D211N RT has 1000-fold higher affinity for $Mn^{2+}$ than wild-type RT. The Hill plot (FIG. 6E) shows the fit of the above activation curves to the Hill equation. Linear regression analysis of each sigmoidal activation curve yielded Hill coefficients ranging from 1.7-2.3, indicating that there are at least two metal-binding sites and that there is positive cooperativity for metal-binding.

Ty1 retrotransposons, like retroviruses, exist as genome parasites within a host cell, and as such, their lifecycle can be influenced dramatically by the host cell environment. They encode an RT that enables transposition by converting the Ty1 transcript into a full-length cDNA copy. RTs and many aspects of the reverse transcription mechanism, mainly base-pairing interactions, require the presence of specific divalent cations, such as $Mg^{2+}$ or $Mn^{2+}$. Cells lacking PMR1 were deficient for Ty1 transposition. Moreover, the transposition phenotype depends on the ability of Pmr1p to transport $Mn^{2+}$, and not $Ca^{2+}$. Thus, it is unlikely that Pmr1p functions directly in the Ty1 lifecycle. Rather, Pmr1p regulates cytosolic $Mn^{2+}$ homeostasis, which subsequently influences one or more aspects of transposition.

Figure 5:
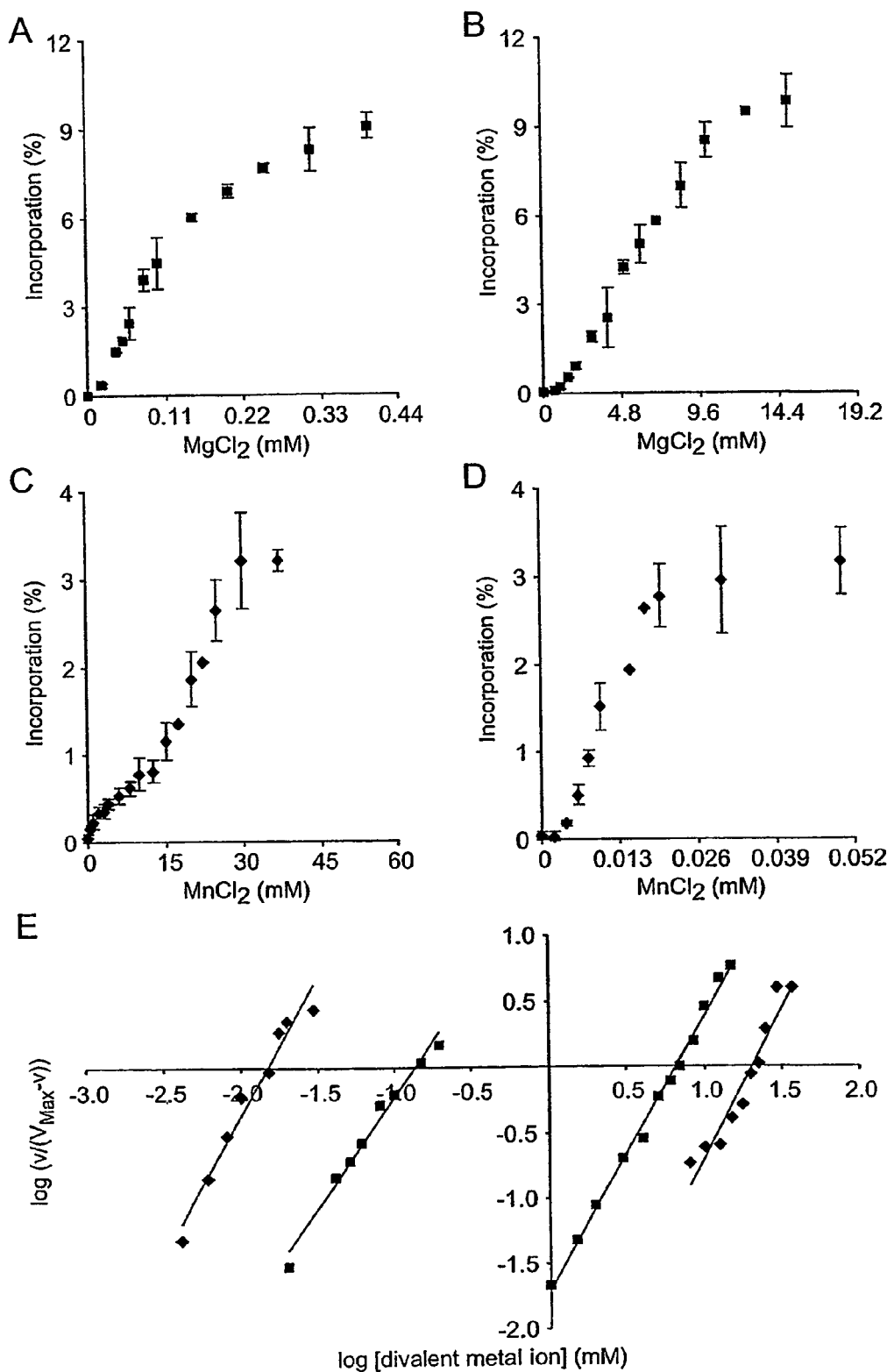
FIG. 5 shows metal-dependent activation of purified recombinant Ty1 RT during RNA-directed DNA polymerization. Specific activity of wild-type RT as a function of total $MgCl_2$ (FIG. 5A) or $MnCl_2$ (FIG. 5C). Specific activity of D211N RT as a function of total $MgCl_2$ (FIG. 5B) and $MnCl_2$ (FIG. 5D). Results are a combination of at least three independent experiments. 100% incorporation corresponds to 137 pmol dGTP incorporated/μg RT during the 60 min assays.

Polymerases and specifically RTs can carry out their enzymatic functions in the presence of $Mg^{2+}$ or $Mn^{2+}$. However, the use of $Mn^{2+}$ instead of $Mg^{2+}$ as a divalent cation tends to decrease the enzymatic activity and the fidelity of these enzymes. Most RTs studied exhibit a preference for $Mg^{2+}$ over $Mn^{2+}$. The enzymatic activity of purified recombinant Ty1 RT with $Mg^{2+}$ was reported to be 3 fold that with $Mn^{2+}$ (Wilhelm et al., supra, 2000). Under saturating conditions of individual metal ions, similar differences in activity with the VLP preparations and purified recombinant Ty1 RTs were observed (FIG. 5; see, also, Table 1, below). However, under more biologically relevant conditions (free divalent cation concentrations less than 6 mM) for wild type Ty1 RT, $Mg^{2+}$-dependent activation was nearly 20-fold higher than that of $Mn^{2+}$-dependent activation (compare FIGS. 5A and 5C).

Ty1 cDNA production was markedly reduced in pmr1Δ cells, while VLP assembly remained unaffected. Moreover, pmr1Δ mutants specifically impaired in $Mn^{2+}$ transport demonstrated a similar defect in cDNA production. These genetic findings indicate that the transposition defect in pmr1Δ mutants is due to accumulation of cytoplasmic $Mn^{2+}$ and subsequent inhibition of reverse transcription of Ty1 RNA into cDNA. Also provided is the first direct kinetic evidence for a dual divalent cation requirement at the active site of a polymerase, specifically an RT; there are at least two metal-binding sites, and positive cooperativity exists between these sites.

Four possible explanations for the Ty1 transposition phenotype of pmr1Δ mutants were considered. 1) alternative activation (homo-ionic activation/hetero-ionic inhibition) based on binding of two metal ions at sites with differential affinitial and effects on catalytic activity (see Table 2, below); 2) the $Mn^{2+}$ accumulation could interfere with primer-template interactions required by the RT to generate a full-length cDNA; 3) the accumulation of $Mn^{2+}$ directly alters the fidelity of the Ty1 RT to such an extent that cDNA synthesis is inhibited; 4) the accumulation of $Mn^{2+}$ could inhibit the activity of the RNase H domain of the RT. The first explanation is favored because of the striking parallels between the crystal structure and sequence comparisons (discussed above) and the biochemical finding that $Mn^{2+}$, but not $Ca^{2+}$, directly inhibited the RT activity of Ty1 RT in vitro even in the presence of excess $Mg^{2+}$. Second, in vivo estimates of divalent metal ions for yeast were considered; the total intracellular concentrations of $Mn^{2+}$ were estimated to be 50 μM in PMR1 cells and 250 μM in pmr1Δ cells (calculated from Lapinskas et al., supra, 1995), while the intracellular concentration of free $Mn^{2+}$ was much less, in the low micromolar range (Ash and Schramm., *J. Biol. Chem.* 257, 9261-9264, 1982; Mandal et al., *J. Biol. Chem.* 275, 23933-23938, 2000). The concentration of free $Mg^{2+}$ in cells is estimated at 0.1-1 mM (calculated from Beeler et al., *Biochim. Biophys. Acta* 1323: 310-318, 1997), while the total $Mg^{2+}$ concentration in yeast cells may be as great as 33 mM (calculated from Graschopf et al., *J. Biol. Chem.* 276: 16216-16222, 2001). The ratio of the estimated free intracellular $Mn^{2+}$ to $Mn^{2+}$ concentrations in yeast (1 μM/1 mM=0.001) falls on the steepest segment of the $Mn^{2+}$ inhibition curve (FIG. 4). However, when an attempt is made to estimate the free $Mn^{2+}$ and $Mg^{2+}$ ion concentrations in wild-type and pmr1Δ yeast cells, a decrease of only 2-4 fold in activity is predicted. A more drastic (20-40 fold) decrease in cDNA synthesis was observed. However, successful completion of cDNA synthesis requires synthesis of 12 kb of DNA and several complex strand transfers and priming events. Therefore, a modest decrease in RT activity could result in a more profound overall cDNA synthesis defect. Third, kinetic studies on the wild-type and D211N Ty1 RTs indicate that at least two highly cooperative metal-binding sites are present in each enzyme (FIG. 5E). Fourth, the D211N mutation affects the affinity for each type of metal ion, but not the overall $V_{Max}$ of the reaction or $K_{cat}$ relative to wild-type RT (Table 1, below). Finally, $Mn^{2+}$ inhibition was observed with purified Ty1, AMV and HIV-1 RT, but not with M-MuLV RT. This result indicates that $Mn^{2+}$ inhibition can be utilized to selectively alter the activity of a subset of all, RTs, and suggests that other divalent cations also may be useful for altering RT activity. Thus, the effect appears to be on the protein and not on the primer-template, arguing against the second explanation. Additionally, the interactions necessary for substrate annealing were likely not affected by the trace amounts of $Mn^{2+}$ with such a large excess of $Mg^{2+}$ present, especially since M-MuLV RT incorporation remained unaffected. While the homopolymer-based RT assay cannot rule out the possibility that $Mn^{2+}$ has additional effects on RT fidelity and/or RNase H activity, for example, by disrupting priming events that occur during strand transfer, the 10-fold reduction in incorporation rate in a homopolymer assay with a single dNTP cannot be explained solely by such an explanation. Preliminary examination of the fidelity of Ty1 RT in wild-type and pmr1Δ mutant cells as well as the affects of $Mn^{2+}$ accumulation on RNase H activity indicates that the accumulation of $Mn^{2+}$ in the pmr1Δ cells alters the in vivo fidelity of the Ty1 RT and also can effect Ty1 RNase H activity.

All possible combinations of high and low affinities for the two metal ions at the A and B sites of RT were modeled, and a single scenario compatible with all of the kinetic data was obtained (Table 2, below). Under conditions where little or no $Mn^{2+}$ was present ($Mn^{2+}$ concentration $<<K_{0.5}$), $Mg^{2+}$ ions occupied both the A and B sites within the RT active site, resulting in a high level of activation (FIGS. 5A and 5B). Similarly, when excess $Mr^{2+}$ was present ($Mn^{2+}$ concentration $>>K_{0.5}$), $Mn^{2+}$ ions occupied both A and B sites, resulting in a low level of activation (FIGS. 5C and 5D). However, when a small amount of Mn was present ($Mn^{2+}$ concentration$\approx K_{0.5}$) for the wild-type RT, the A site was likely occupied by a $Mg^{2+}$ ion, and the B site likely contained a tightly-bound $Mn^{2+}$ ion, resulting in a low level of activation or inhibition (Table 2). On the other hand, when a small amount of $Mn^{2+}$ was present ($Mn^{2+}$ concentration$\approx K_{0.5}$) for the D211N RT, the A site was likely occupied by a $Mn^{2+}$ ion, and the B site likely contained a $Mg^{2+}$ ion, which resulted in a high level of activation. These predictions are based on the fact that increasing amounts of $Mn^{2+}$ inhibited the wild-type RT (FIG. 4), but not the D211N RT (FIG. 4D). The D211N mutation appeared to dramatically bias the divalent cation affinity at the A site toward $Mn^{2+}$, allowing $Mg^{2+}$ to saturate the B site. The peak in activity at intermediate levels of $Mn^{2+}$ (FIG. 4D) was likely due to the saturation of the A site with $Mn^{2+}$, and the presence of $Mg^{2+}$ at the B site. Based on the present data, it is predicted that the higher affinity site for $Mn^{2+}$ (the B site) in the wild-type RT has the greatest impact on the $V_{Max}$ of the enzymatic reaction. When $Mg^{2+}$ is bound, a high $V_{Max}$ is obtained, and when $Mn^{2+}$ is bound, a lower $V_{Max}$ can occur because the smaller $Mg^{2+}$ ion at the B site interacts more favorably than a $Mn^{2+}$ ion sterically with the pyrophosphate leaving group and the enzyme. To explain the reversal of metal ion affinities that occurred by replacing the aspartate at position 211 with asparagine (FIG. 1), it is likely that the D211N mutation provides a nitrogen ligand to the A site metal, which $Mn^{2+}$ is much more likely than $Mg^{2+}$ to coordinate (Bock et al., *J. Amer. Chem. Soc.* 121, 7360-7372, 1999). Tighter $Mn^{2+}$ binding can result from avoiding the clustering of too many anionic ligands near the metal.

In summary, Pmr1p was identified as an indirect host factor involved in Ty1 retrotransposition. Mutations in PMR1 that specifically abolished $Mn^{2+}$ (but not $Ca^{2+}$) transport decreased the frequency of Ty1 transposition to the same extent as a complete deletion of PMR1. Moreover, deletion of PMR1, or simply the lack of $Mn^{2+}$ transport, dramatically decreased the relative amount of Ty1 cDNA produced in vivo.

In addition, low levels of $Mn^{2+}$ relative to $Mn^{2+}$ dramatically inhibited RT activity associated with Ty1 VLPs, as well as purified recombinant Ty1 RT, AMV RT and HIV-1 RT in vitro. Since Pmr1p regulates cytosolic $Mn^{2+}$ homeostasis, the present results indicate that accumulation of $Mn^{2+}$ in pmr1D cells inhibits the steps required to reverse transcribe the Ty1 RNA into the cDNA copy of the element, thus providing a previously undescribed target for affecting RT activity and, therefore, retroviral replication in cells by perturbing cytoplasmic metal ion concentrations in a target cell. These present results also reinforce the importance of metal ion clusters in catalysis, and support the concept that targeting such clusters can be useful for identifying viral replication inhibitors (Filler and Lever, supra, 1997).

EXAMPLE 2

High Throughput Screening Assay for Agents that Alter Manganese Trasporter Activity This example provides a high throughput assay using yeast cells transformed to express a human Prm1 divalent cation transporting protein.

As disclosed in Example 1, the yeast retrovirus-like element Ty1 cannot replicate in pmr1 mutant of yeast due to defective pumping of manganese ion by the mutant Pmr1 transporter. Elevated $Mn^{2+}$ concentration in the mutant cells interferes with reverse transcription through combined effects on the RT and RNAse H activities, and in vitro studies demonstrated that HIV-1 RT, like Ty1 RT, also is exquisitely sensitive to inhibition by manganese ion (Example 1); Pmr1p is highly conserved from yeast to man.

This Example provides a drug screening assay using living yeast cells to facilitate identification of agents that alter manganese ion transport of a human Pmrp transporter, thus providing a drug that can mimic the effect of the mutant Pmrp1 transporter and can be useful as to inhibit retrotransposable element replication, for example, HIV-1 replication, wherein the agent can be useful for immune restoration in AIDS patients. Using the disclosed high throughput assay, agents that interfere with the manganese transporting function of the human Pmr1 transporter protein can be identified. Such agents that can be examined in vitro to confirm they affect the human (or yeast) Pmr1p in vitro, then can be further examined for the ability to inhibit HIV multiplication in a single round infection assay (Roos et al., *Virology* 273: 307-315, 2000, which is incorporated herein by reference) or using a p24-based multiplication assay.

The exemplified assay, which utilizes a 96 well based format to examine yeast cell growth in the presence or absence of test agents, is based on the requirement of an sod1 mutant yeast cell of lysine and methionine for growth in aerobic medium, whereas an sod1 pmr1 double mutant does not have such requirements. There are enzymes in the lysine and methionine biosynthetic pathways that are super-sensitive to superoxide anion and associated free radicals (Lapinskas et al., supra, 1995). The basis of the present assay is that elevated redox-active $Mn^{2+}$ ion in the sod1 pmr1 double mutant can act as a "chemical" SOD activity in pmr1 mutants such that the pmr1 mutation suppresses the damage caused by superoxides and related free radicals.

Compound screen. A yeast strain was constructed having a genotype including sod1::kanAMpmr1::hygAMX uar3. This strain was separately transformed with two URA3 centromeric yeast vectors, one expressing human Pmr1 (EBY 115c) and the other an empty vector (EBY116B), which serves as a positive control for growth. Test agents that allow the hPmr1p strain grow as well as this positive control strain are selected as drug candidates useful for inhibiting RT activity and retroviral multiplication.

A Hydra®-96 FlexChem® Microdispenser liquid handling robot (Apogent Discoveries; Hudson N.H.) to assemble 96 well plates containing 0.1 ml aliquots of medium seeded with approximately 100 cells of the appropriate genotype. The medium is a minimal medium lacking lysine, methionine and uracil, the latter to select the hPmr1p plasmid. The medium also can contain hygromycin and carbenicillin, if necessary, to prevent contaminants from growing. Four ul aliquots of test agent (approximately 400 uM in DMSO) from the PRIME-Collection 2000™ combinatorial library (Chembridge Corp.; San Diego Calif.) or selected from the ChemBridge™ Master Database, for example, are added to a well; duplicates, triplicates, and/or examination of a test agent at two or more concentrations also can be included. Typical hit rates for transporters in assays similar to the present assay range from about 1 in 1000 to 1 in 10,000. The use of the Hydra®-96 FlexChem® Microdispenser liquid handling robot to aliquot the test agent, mix the test agent with the culture, dilute the drug, etc., minimizes the amount of labor and the likelihood of pipetting errors. Using the exemplified assay, a team of two people can process several thousand compounds per week.

Under the growth conditions, there is a 48 to 72 hr delay between the time when the control strain (the one without hPmr1p) grows to a maximal optical density and when the experimental strain grows. This period of times provides an excellent dynamic range such that, even if a drug that is only, for example, about 10% effective, the assay can allow identification of the activity. The readout for growth is performed using a 96 well spectrophotometer, can incorporate a computerized output with an algorithm for subtracting background. For example, each 96 well plate can contain 80 test agents, one in each well of columns 2 to 11, and solvent alone in columns 1 and 12, such that the wells of columns 1 and 12 can be averaged and the mean background can be automatically subtracted from each well. All of the growth data can be monitored several times over the 48 to 72 hr period, thus allowing a determination of the growth kinetics.

Primary positives that are identified can be further examined in a battery of secondary assays. First, the growth test can be repeated using a broader range of test agent concentrations. Second, positives can be further tested against a similar strain to that described above, but containing a wild-type SOD1 gene. Loss of PMR1 function makes cells supersensitive to growth in high $Mn^{+2}$ ion, thus providing a second simple growth test that can be performed in the presence of various drug concentrations. If desired, additional yeast strains can be made containing the yeast Pmr1 (or other Pmr1 transporter) instead of the human Pmr1p. Positive test agents also can be examined for the ability to interfere with Ty1 retrotransposition in strains expressing yeast or human Pmr1 protein.

A number of negative controls can be performed, either in separate assays or in parallel with any particular assay, including, for example, addition of the vehicle in which the compounds are suspended (DMSO) added alone to the wells. Positive controls include supplementation of the medium with uracil, which allows loss of the PMR1 plasmid and luxuriant growth (as would be expected for a positive test agent). No inhibitors of hPMR1 or yeast PMR1 have not previously been identified and, therefore, such a positive control compound that directly inhibits the transporter is not available.

In vitro testing of identified agents. Positive agents identified using the above described screening assay can be further examined in vitro for the ability to alter manganese ion transport. As assays similar to that used to detect the transport of $Ca^{2+}$ into vesicles isolated from yeast cells expressing either yeast or human Pmr1 protein (Sorin et al., *J. Biol Chem.* 272: 9895-901, 1997; Ton et al., *J. Biol. Chem.* 277: 6422-6427, 2002, each of which incorporated herein by reference) can be used to measure manganese transport. The described assay is based on import of $^{45}Ca^{2+}$ into vesicle isolated from the yeast cells. This in vitro assay can be used to examine whether the effect of any agent identified in the screening assay is a direct effect on the Pmr1p, or can be used to determine whether the agent is active specifically against the human Pmr1p transporter, or whether in more generally effects, for example, the yeast and human Pmr1p transporters.

Testing compounds for anti-HIV-1 activity. A simple single-round infection assay based on the activation of an SIV LTR-luciferase reporter gene can be used to determine whether an identified agent can inhibit HIV-1 RT activity (Roos et al., supra, 2000). As the drug is predicted to affect the reverse transcription step, it would be expected to be active only in the target cell and not in the producer cells. The luciferase assay can easily be carried out in a high throughput format. Further, any positives identified in the single-round infection assay can be examined using a multi-round assay, for example, a p24 assay (or RT assay) following a low multiplicity of infection (MOI). Methods of performing p24 assays and RT assays are well known and routine in the art (see, for example, Goff et al., *J. Virol.* 38: 239-248, 1981, which is incorporated herein by reference; describing an RT assay), and can be performed, for example, using commercially available kits (e.g., an Alliance® HIV p24 RIA kit; Perkin Elmer; prod. no. NEK040001KT).

Although the invention has been described with reference to the above example, it will be understood that modifications and variations are encompassed within the spirit and scope of the invention. Accordingly, the invention is limited only by the claims, which follow Tables 1 and 2.

TABLE 1

Kinetic Constants of Metal Activation of Wt. and D211N Ty1 Reverse transcriptases

| Ty1 RT | $_n$Mg2+ | $_n$Mn2+ | $K_{0.5}Mg^{2+}$ (mM) | $K_{0.5}Mn^{2+}$ (mM) | $k_{cat}Mg^{2+}$ (hr$^{-1}$) | $k_{cat}Mn^{2+}$ (hr$^{-1}$) |
|---|---|---|---|---|---|---|
| Wt. | 1.7 ± 0.1 | 2.3 ± 0.2 | 0.13 ± 0.04 | 19.9 ± 1.6 | 1.61 ± 0.32 | 0.56 ± 0.07 |
| D211N | 2.1 ± 0.1 | 2.1 ± 0.1 | 6.3 ± 0.2 | 0.02 ± 0.003 | 1.60 ± 0.28 | 0.57 ± 0.03 |

TABLE 2

Proposed divalent cation binding affinities and activities for RTs

| A site | B site |
|---|---|
| Wt. Ty1 RT | |
| very low affinity for $Mn^{2+}$ | high affinity for $Mn^{2+}$ |
| very high affinity for $Mg^{2+}$ | low affinity for $Mg^{2+}$ |
| D211N Ty1 RT | |
| very high affinity for $Mn^{2+}$ | high affinity for $Mn^{2+}$ |
| very low affinity for $Mg^{2+}$ | low affinity for $Mg^{2+}$ | metal activation of Ty1 RT

| A site | + | B site | = | activity | comment |
|---|---|---|---|---|---|
| $Mg^{2+}$ | | $Mg^{2+}$ | | high | |
| $Mg^{2+}$ | | $Mn^{2+}$ | | low | unlikely for D211N |
| $Mn^{2+}$ | | $Mg^{2+}$ | | high | unlikely for Wt. |
| $Mn^{2+}$ | | $Mn^{2+}$ | | low | |

What is claimed is:

1. A method of identifying an agent that reduces the activity of reverse transcriptase comprising:
   a) contacting a cell comprising a divalent cation transporting protein with a test agent;
   b) detecting a change in the concentration of intracellular manganese ions in the cell after contact with the test agent as compared to the concentration of manganese ion levels in the absence of the test agent; and
   c) detecting reverse transcriptase activity in the cell using a polyribonucleotide or polydeoxyribonucleotide template for reverse transcriptase activity, wherein an increase in the concentration of intracellular manganese ions in the cell after contact with the test agent, and a decrease in activity of reverse transcriptase is indicative of an agent that reduces the activity of reverse transcriptase.

2. The method of claim 1, wherein the cell comprises an isolated cell membrane.

3. The method of claim 2, wherein the cell membrane comprises a eukaryotic cell membrane.

4. The method of claim 3, wherein the eukaryotic cell membrane comprises a yeast cell membrane or a mammalian cell membrane.

5. The method of claim 3, wherein the eukaryotic cell membrane comprises a human cell membrane.

6. The method of claim 1, wherein contacting the cell comprises contacting a cell comprising a cell membrane.

7. The method of claim 6, wherein the cell comprises a yeast cell.

8. The method of claim 6, wherein the cell comprises a human cell.

9. The method of 6, wherein the cell comprises a T lymphocyte.

10. The method of claim 1, wherein the cell comprises a divalent cation transport protein comprising an ATPase.

11. The method of claim 1, wherein the cell comprises a divalent cation transport protein comprising a P-type ATPase.

12. The method of claim 11, wherein the ATPase is a Pmr1p protein or a homolog thereof.

13. The method of claim 1, wherein the test agent does not alter transport of a divalent cation other than manganese ions by a divalent cation transporting protein.

14. The method of claim 1, wherein the agent reduces or inhibits manganese ion transport out of a cell.

15. The method of claim 1, wherein the polyribonucleotide or polydeoxyribonucleotide template comprises a nucleotide sequence of a retrotransposable element, and wherein further the retrotransposable element is a human immunodeficiency virus (HIV).

16. The method of claim 1, wherein the polyribonucleotide or polydeoxyribonucleotide template comprises a nucleotide sequence of a retrotransposable element, and wherein further the retrotransposable element is a Ty retrotransposon.

* * * * *

UNITED STATES PATENT AND TRADEMARK OFFICE
CERTIFICATE OF CORRECTION

PATENT NO. : 7,601,489 B2
APPLICATION NO. : 10/507252
DATED : October 13, 2009
INVENTOR(S) : Boeke et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 705 days.

Signed and Sealed this

Fifth Day of October, 2010

David J. Kappos
*Director of the United States Patent and Trademark Office*